US012237150B2

(12) United States Patent
McKenzie et al.

(10) Patent No.: US 12,237,150 B2
(45) Date of Patent: Feb. 25, 2025

(54) PLASMA ION PROCESSING OF SUBSTRATES

(71) Applicant: Lifehouse Australia as Trustee for The Lifehouse Australia Trust, Camperdown (AU)

(72) Inventors: David R. McKenzie, Sydney (AU); Marcela Bilek, Sydney (AU); Aleksey Kondyurin, Sydney (AU); Elena Kosobrodova, Sydney (AU)

(73) Assignee: LIFEHOUSE AUSTRALIA AS TRUSTEE FOR THE LIFEHOUSE AUSTRALIA TRUST, Camperdown (AU)

( * ) Notice: Subject to any disclaimer, the term of this patent is extended or adjusted under 35 U.S.C. 154(b) by 161 days.

(21) Appl. No.: 17/769,724

(22) PCT Filed: Oct. 16, 2020

(86) PCT No.: PCT/AU2020/051117
§ 371 (c)(1),
(2) Date: Apr. 15, 2022

(87) PCT Pub. No.: WO2021/072502
PCT Pub. Date: Apr. 22, 2021

(65) Prior Publication Data
US 2022/0359163 A1    Nov. 10, 2022

(30) Foreign Application Priority Data
Oct. 16, 2019   (AU) .................................. 2019903902

(51) Int. Cl.
*H01J 37/32*   (2006.01)
*A61L 27/16*   (2006.01)
(Continued)

(52) U.S. Cl.
CPC ........ *H01J 37/32412* (2013.01); *A61L 27/16* (2013.01); *A61L 27/18* (2013.01);
(Continued)

(58) Field of Classification Search
CPC .......... A61L 27/34; A61L 27/50; A61L 31/14; A61L 33/0041; H01M 50/417; H01J 37/32412
See application file for complete search history.

(56) References Cited

U.S. PATENT DOCUMENTS

| | | | | |
|---|---|---|---|---|
| 2001/0007083 A1* | 7/2001 | Roorda | ............... | A61L 33/0041 623/1.15 |
| 2010/0129422 A1* | 5/2010 | Han | ........................ | A61L 27/50 424/426 |

FOREIGN PATENT DOCUMENTS

| | | | | |
|---|---|---|---|---|
| EP | 0803342 A1 * | 4/1997 | ............. | B29C 59/10 |
| WO | WO-9904411 A1 * | 1/1999 | ............. | B29C 59/14 |

(Continued)

OTHER PUBLICATIONS

The International Preliminary Report on Patentability of the International Bureau for WIPO for PCT Application No. PCT/AU2020/051117 issued Apr. 19, 2022, 6 pages.
(Continued)

*Primary Examiner* — Dah-Wei D. Yuan
*Assistant Examiner* — Andrew J Bowman
(74) *Attorney, Agent, or Firm* — Womble Bond Dickinson (US) LLP

(57) ABSTRACT

A method for plasma ion processing is described, including flowing a gas into porous material; and exposing the gas to a pulsed electric field whilst the gas is in the pores. The pulsed electric field ionises the gas to generate a plasma. The method may additionally include exposing the porous material to a gas so as to generate functionality. The method may (Continued)

additionally include exposing the functionalised porous material to a functional species so as to covalently attach said functional species to the surfaces of the pores.

16 Claims, 21 Drawing Sheets

(51) Int. Cl.
| | |
|---|---|
| A61L 27/18 | (2006.01) |
| A61L 27/56 | (2006.01) |
| B29C 64/30 | (2017.01) |
| B29C 71/04 | (2006.01) |
| B33Y 40/20 | (2020.01) |
| C08J 7/12 | (2006.01) |
| B22F 1/145 | (2022.01) |

(52) U.S. Cl.
CPC .............. *A61L 27/56* (2013.01); *B29C 64/30* (2017.08); *B29C 71/04* (2013.01); *B33Y 40/20* (2020.01); *C08J 7/123* (2013.01); *B22F 1/145* (2022.01); *C08J 2355/02* (2013.01); *C08J 2367/04* (2013.01); *C08J 2371/12* (2013.01); *C08J 2381/06* (2013.01); *H01J 37/32541* (2013.01); *H01J 2237/3365* (2013.01)

(56) References Cited

FOREIGN PATENT DOCUMENTS

| | | | | |
|---|---|---|---|---|
| WO | 0204083 A2 | 1/2002 | | |
| WO | WO-03020425 A1 * | 3/2003 | ........... | G01N 33/521 |
| WO | 2007032321 A1 | 3/2007 | | |
| WO | WO-2009015420 A1 * | 2/2009 | ........... | A61L 27/042 |

OTHER PUBLICATIONS

The International Search Report of the International Searching Authority for PCT Application No. PCT/AU2020/051117 mailed Nov. 26, 2020, 5 pages.

The Written Opinion of the International Searching Authority for PCT Application No. PCT/AU2020/051117 mailed Nov. 26, 2020, 5 pages.

* cited by examiner

PLASMA ION PROCESSING OF SUBSTRATES

CROSS-REFERENCE TO RELATED APPLICATIONS

The present application is a US national phase application under 35 USC 371 of international application no. PCT/AU2020/051117, filed 16 Oct. 2020, which claims priority to Australian Patent Application No. 2019903902, filed 16 Oct. 2019, entitled "Plasma Ion Processing of Substrates."

FIELD

The present disclosure relates to the field of plasma ion processing of substrates to modify surface characteristics of the substrate.

BACKGROUND

Plasma immersion ion implantation (PIII) treatment can be used to change the structure of polymers. The changed structure has been reported to provide improvements in wear resistance, adhesiveness, chemical resistance and biocompatibility. PIII treatment may also provide increased wettability of the surface, a high protein binding capacity and improved bacterial properties.

SUMMARY

In some embodiments, there is provided a method for plasma ion processing, for example functionalising, a porous material, comprising: a) flowing a gas into it where it remains stationary, or optionally maintaining its flow through, pores of said porous material; and b) exposing said gas to a pulsed electric field whilst said gas is in said pores; wherein the pulsed electric field is of sufficient strength to ionise said gas to generate a plasma, at least for short periods after the pulsed electric field is applied.

In some embodiments the gas is passed continuously through said pores during step b) at a constant or time varying rate at a pressure that is constant in time or is time varying. Alternatively the gas may remain static in said pores during step b) at a constant or almost constant pressure.

The method may additionally comprise step c), after step b), of exposing the porous material to a gas, optionally a gas comprising oxygen or mixtures thereof with other gases, or a gas comprising nitrogen or mixtures thereof with other gases, or a gas containing, methane, acetylene or other carbon or hydrocarbon containing gases and mixtures thereof and with other gases, so as to generate functionality, optionally oxygen-containing, nitrogen-containing or carbon-containing functionality, or mixtures thereof, on surfaces of the pores. It may comprise step d), after step b) (optionally after step c) in the event that step c) is conducted), of exposing the functionalised porous material to a functional species so as to covalently attach said functional species to the surfaces of the pores. The functional species may be a labelling molecule, a bioactive molecule, a biological molecule, a cell, a micelle, a liposome, a polymer particle, a hydrogel a nanoparticle or some other type of functional species.

The gas of step a) may be, or may comprise, any of the following: nitrogen, oxygen hydrogen, helium, argon, ammonia or water vapour. It may be, or may comprise, acetylene, methane, ethylene or any carbon-containing or any organic gas. A downstream pressure of the gas may be less than about 5 mTorr. The mean pressure within the material during step b) may be given by the formula $P=k/d$, where P is the mean pressure, k has a value between about $10^{-5}$ and about $10^{-1}$ Torr·m and d is the diameter of the smallest pore to be functionalised using the method. The possible values of Pd for successful treatments depend on the dielectric constant of the porous scaffold and on the voltage used in the treatment.

In some embodiments, the value of k is that where the voltage needed to breakdown the gas to create a plasma, is a minimum. As Pd moves away from this value in either direction, higher and higher voltages are required to breakdown the gas as per Paschen's law. There are a number of effects that can act to reduce the breakdown voltage required compared to that predicted by Paschen's law. One is increasing the frequency of the voltage pulses. As the off time between pulses becomes shorter there are more charged species remaining in the afterglow of the previous pulse that can contribute to the initiation of the discharge in a subsequent pulse. The voltage required for breakdown of the gas to create a plasma can also be reduced for any given set of operating conditions if a material with a higher secondary electron emission coefficient is being treated. The increased secondary electron emission coefficient increases the number of electrons emitted from the surface for each ion impact during the discharge resulting in a denser more rapidly growing discharge. The field created in the voids for any given applied voltage will also be enhanced as the dielectric constant of the material being treated increases. Enhancements such as those provided by increased frequency, increased secondary electron yield and increased field due to increased dielectric constant of the material being treated will widen the operable range of k.

The pulsed electric field may be generated by a potential of least about 0.5 kV. It may have a pulse frequency of 10 Hz to about 20 kHz. It may have pulses of about 10 to about 500 microseconds in duration. In some instances the pulsed electric field may be bipolar, i.e. it may be directed in one direction and then in the opposite direction at different times. A change in the direction of the field may be useful for neutralizing accumulated surface charge.

The porous material may comprise, or may consist essentially of, a polymer, e.g. a member of the PAEK family or polycaprolactone (PCL), Nylon, ABS or a resin, polyethylene, polystyrene, polyurethane, polypropylene, PVC, PLA or PDMS. The pores of the porous material may have a mean diameter of about 0.1 to about 5000 micrometres. The porous material may be a fabric or a structure consisting of overlaid linear elements forming a structure known as a "woodpile" or a structure consisting of packed hollow tubes with their axes parallel or arranged in a stacked structure such as a woodpile structure. The packed hollow tubes may be flexible and made of a polymer such as PVC, polyurethane, PDMS, polyethylene, or polypropylene.

Step a) may comprise passing the gas through an inlet tube to the porous material. Step b) may comprise applying a negative bias of at least −0.5 kV between a first electrode and a second electrode, wherein the first electrode, being negatively biased, at least partially surrounds, or optionally completely surrounds, the porous material. The mutual capacitive coupling of the surface of the pore to the first or active electrode to which the negative voltage pulses are applied may be less than but comparable to or larger than the mutual capacitive coupling of the surface of the pore to the second electrode.

The pulsed electric field may be generated by a pulsed potential which is applied between the first electrode, negatively biased, and the second electrode, the second electrode optionally being earthed. The second electrode may be disposed at least in part within the porous material. The second electrode may form part of, or may be disposed on, or connected to a containment vessel in which the negatively biased first electrode and the porous material are located. The second electrode may be directly accessible to the plasma so that electrons and or ions of the plasma may directly bombard the second electrode. The second electrode may be in the form of an annulus and may be coupled to the gas inlet and/or to an outlet tube.

The porous material may be a scaffold for tissue engineering or part of a column for separating or extracting a target molecular species from solution. It may be a powder for medical diagnostics or drug delivery.

In some embodiments there is provided a method for plasma ion processing, for example functionalising, a porous material, comprising: a) flowing a gas into pores of said porous material; b) exposing said gas to a pulsed electric field whilst said gas is in said pores; and c) exposing the porous material to a gas comprising oxygen, nitrogen, ammonia water vapour or any carbon containing gas so as to generate oxygen-containing, nitrogen-containing or carbon-containing functionality on surfaces of the pores; wherein the pulsed electric field is of sufficient strength to ionise said gas to generate a plasma.

In some embodiments there is provided a method for plasma ion processing, for example functionalising, a porous polymer material, comprising: a) flowing nitrogen through pores of said porous polymer material; and b) exposing said nitrogen to a pulsed electric field of frequency about 10 Hz to 20 kHz with a pulse duration of about 10 to 500 microseconds whilst said gas is in said pores; wherein the pulsed electric field is of sufficient strength to ionise said gas to generate a plasma.

In some embodiments there is provided a method for functionalising a porous polymer material, comprising: a) flowing nitrogen through pores of said porous polymer material; and b) exposing said gas to a pulsed electric field generated by a negative bias of at least −0.5 kV applied between a negatively biased first electrode and an earthed second electrode whilst said gas is in said pores; wherein the pulsed electric field is of sufficient strength to ionise said gas to generate a plasma and wherein the negatively biased first electrode at least partially, optionally completely, surrounds the porous material.

In some embodiments there is provided an apparatus for plasma ion processing, for example functionalising, a porous material, comprising:
 a) a first electrode and a second electrode;
 b) a power supply coupled between the first electrode and the second electrode for providing a pulsed potential between the first and second electrodes such that the first electrode is negatively biased relative to the second electrode;
 c) a support for holding the porous material;
 d) an inlet tube coupled to said support such that a gas passing through the inlet tube is constrained to pass into pores of the porous material;
 e) a gas supply for supplying an ionisable gas to said inlet tube; and
 f) a pump for applying a partial vacuum downstream of the support;
 wherein the first electrode is disposed so that, when the support holds the porous material, the first electrode at least partially surrounds the porous material; and
 wherein the power supply is capable of providing a pulsed electric field of sufficient strength to ionise the gas to generate a plasma.

In some embodiments, the second electrode is earthed. Alternatively the first electrode may be earthed.

In some embodiments the support is in the form of a sleeve in which the porous material is constrained in use.

The first electrode may be the sleeve, or may be disposed on the sleeve, or may at least partially surround the sleeve. The first electrode may be a sleeve surrounding the containment vessel which in turn surrounds the porous material.

The apparatus may additionally comprise a containment vessel in which the support and the first electrode are located. The second electrode may form part of the containment vessel, may be connected to or may be disposed on a wall of the containment vessel. The pump may be coupled to said containment vessel so as to be capable of applying a partial vacuum in said containment vessel.

The power supply may be such that, when a porous material is located in the support and a pulsed electric field is generated by a potential between the first and second electrodes, said electric field is of sufficient strength within the porous material as to cause ionisation of a gas in the porous material so as to generate a plasma.

In an embodiment there is provided an apparatus for plasma ion processing a porous material, comprising:
 a) a first electrode and a second electrode;
 b) a power supply coupled to the first electrode and/or the second electrode for providing a pulsed potential between the first and second electrodes such that the first electrode is negatively biased relative to the second electrode;
 c) a support for holding the porous material, said support being in the form of a sleeve, and said first electrode being the sleeve, or being disposed on the sleeve or at least partially surrounding the sleeve;
 d) an inlet tube coupled to said support such that a gas passing through the inlet tube is constrained to pass into pores of the porous material;
 e) a gas supply for supplying an ionisable gas to said inlet tube;
 f) a pump for applying a partial vacuum downstream of the support; and
 g) a containment vessel in which the support and the first electrode are located, the second electrode forming part of the containment vessel, being connected to the containment vessel or being disposed on a wall of the containment vessel and the pump being coupled to said containment vessel so as to be capable of applying a partial vacuum in said containment vessel;
 wherein the power supply is capable of providing a pulsed electric field of sufficient strength to ionise the gas to generate a plasma.

In some embodiments there is provided a method of plasma ion processing a porous material comprising the steps of:
 a) providing an apparatus according to the second aspect;
 b) loading the porous material into the support;
 c) passing an ionisable gas from the gas supply through the inlet tube into pores of the porous material;
 d) applying a partial vacuum downstream of the porous material; and
 e) providing a pulsed potential between the first and second electrodes by means of the power supply so that the first electrode is sufficiently negatively biased relatively to the second electrode, so as to ionise said gas so as to generate a plasma.

In some embodiments, there is provided a method of plasma modification of a porous material, the method comprising:
    locating the porous material in an electric field between electrodes so as to impart to the internal and/or external surfaces of the porous material an electric potential;
    generating, from a gas provided within the porous material, a plasma at the porous material, wherein the plasma is an electrically conductive medium between the electrodes; and
    providing the gas at pressure that results in ions of the plasma implanting in the porous material under the force of the electric field.

BRIEF DESCRIPTION OF DRAWINGS

FIG. 231 shows a 3D printed scaffold in column form: A) without a shell and sealing; B) with a shell and sealing. C) The scaffold in mesh form.

In FIG. 26B the inner ring about the scaffolds is a 200 μm thick inbuilt tubular outer shell; the outer ring about the scaffolds is a silicone sealing tube (10×11 cm).

DESCRIPTION OF EMBODIMENTS

Figure 1:
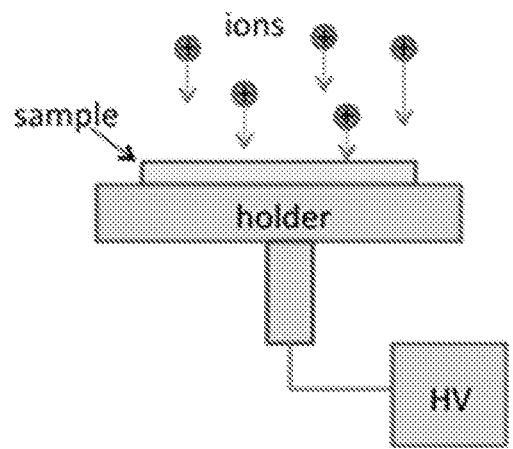
FIG. 1: A diagram illustrating a process for plasma functionalisation of surfaces. Nitrogen ions accelerated to a sample surface from a plasma by a pulsed voltage of 20 kV applied to the holder. The holder is mounted in a grounded vacuum chamber and the positive terminal of the high voltage pulsed power supply (HV) was connected to the second electrode (not shown), which was at ground potential.

The term "porous", as used herein, is used in its broadest sense, to indicate the presence of continuous channels, referred to herein as "pores", through the substance. A porous substance may be a cohesive structure containing holes, e.g. an open celled foam, or may be a particulate material wherein the pores represent the spaces between the particles, and optionally also holes within particles.

Thus for the purposes of this invention, a porous structure is any arrangement of a solid material and void spaces that may be filled with gas. The void spaces may be partly or fully connected to form at one extreme, particles suspended in a gas and at the other extreme a system of connected pores penetrating an otherwise solid object. In the case where particles are suspended in a gas, vibration may be provided to maintain the void spaces. The solid component of the porous structure may comprise, or may consist of, a wide variety of materials including ceramics, metals and polymers, as well as mixtures and blends thereof. The porous material may comprise an assembly of components, such as membranes, powder granules, fibres, or beads. The porous material may be a woven fabric or a non-woven fabric or a structure made by additive manufacturing.

The term "material" as used herein should be taken to include substances comprising a single chemical entity as well as mixtures and blends of substances. For example a homogeneous blend of two polymers is considered a "material" as is a phase separated mixture or a fabric comprising threads of different polymers. Another example of a "material" as the term is used herein would be a particulate material in which the particles have a core-shell structure in which a core of a first substance is coated by a shell of a different substance or a particulate material comprising particles having different chemical compositions.

The term "[A] at least partially surrounds [B]" is used to indicate that there is a straight line between two points on A which passes through some point in B. The term "[A] completely surrounds [B]" indicates that each point in B lies on a straight line between two points on A.

In the context of the present invention, the term "comprise" and related terms should be taken to indicate the presence of the specified integer(s) but not to preclude the presence of other (unspecified) integers. It does not imply that the specified integer(s) are present in greater quantity than any unspecified integers. The term "consist" and related terms should be taken to indicate the presence of the specified integer(s) to the exclusion of any other intentionally present integers. Thus for example small amounts of unintended impurities, unspecified, may nevertheless be present.

The terms "about" and "approximately" should be taken to include a margin of +/−10% unless the context indicates otherwise.

Currently available in vitro environments for cell culture are typically far removed from those in vivo, hampering the ability to accurately screen drugs prior to clinical trials (9 out of 10 fail in trials); to grow replacement tissues and organs in the laboratory and to extract reliable predictions of in vivo responses based on in vitro studies. Technology platforms that enable the fabrication of synthetic environments which better mimic the hierarchical structure, mechanics and biochemical complexity of natural tissues would remove these impediments and facilitate major progress in the biological sciences and medicine.

Increasingly research in cell biology is showing that cells respond to a complex combination of cues from their environment including the chemistry, topography and the mechanical properties of proximate structures as well as the dimensionality and structure of their surroundings. The coupling of these cues determines the behaviour of the cells such that the same cells in different microenvironments often respond to the external stimuli differently. Plasma immersion ion implantation (PIII) treatment is an effective method of surface modification for polymers, which can provide advantages in biomedical applications such as wound dressings, biomedical implants including dental implants, tissue engineering, cell expansion platforms and cell/drug delivery systems.

However, many of these biomedical applications may be served or better served using 3D structures with internal porosity such as scaffolds, beads in suspension and capillary bundles. At least some methods of PIII treatment are not well suited to such structures.

Scaffold development in tissue engineering can use metals such as titanium, natural and synthetic hydrogels as well as thermoplastic polymers, including the high melting point polymer family polyaryletherketone (PAEK), such as typical members polyetheretherketone (PEEK), polyetherketone (PEK), polyetherketoneketone (PEKK) and polyetherketoneether (PEKE) and the bioresorbable polymer PCL (polycaprolactone), which allow structures to be created using technologies often referred to as additive manufacturing, filament deposition modelling, selective laser sintering or 3D printing. Applying these fabrication technologies to create structures in polymers and metals shows promise in creating hierarchical structures with provision of internal pores, often interconnected and external structured or textured surfaces that mechanically mimic in vivo tissue environments. Synthetic scaffold surfaces typically need to be modified to make them biocompatible and to allow functionalisation with biomolecules that communicate with cells via receptors in the cell membranes. Current technologies for functionalisation utilise multiple wet chemistry steps often involving complex protocols that utilise solvents and potentially toxic reactants making the processes commercially unattractive and often unsuitable for regulatory approval.

Complex interconnected 3D structures are also important in applications which require surface areas to be maximised so that interactions between species in solution and species on the surface can be optimised. Examples include the use of enzymes in continuous flow processes for chemical, food or biofuel processing in which there is flow of a medium containing the reactants over surfaces bearing the enzymes that are tethered to them. Similarly, the sensitivity of a biosensing process in which a sensing molecule, such as an antibody, is tethered to a surface is enhanced by maximising available interaction areas where the immobilised biological detection agents are tethered in such a way that they can bind selectively to their targets.

Certain embodiments disclosed herein relate to a dry plasma processing approach to activate complex interconnected 3D polymeric networks that enables direct covalent immobilisation of, for example, bioactive molecules from buffer solution. The bioactive molecules can be applied very simply and safely by immersion, spotting or painting on of a solution of the bioactive molecule. Since it is thought that the covalent immobilisation is facilitated by reactive radicals created in the scaffold structures by the plasma activation process, the solution pH can be varied to manipulate the charges on the molecules and on the surface to achieve a desired orientation of the bioactive molecules as they arrive at the surface to be covalently coupled. Once covalently linked these preferred orientations are locked in.

Aspects of the disclosure may be described as follows. A first electrode in proximity to the object or objects to be treated and a second electrode is located elsewhere, for example on a connecting tube that connects to the region containing the objects to be treated (which are enclosed within the first electrode). The first electrode at least partially surrounds the object or objects to be treated. In a pulsed operation, the first electrode is initially made negative relative to the second electrode by an applied potential. As a result, gas connecting the region inside the first electrode to the region inside or in connection with the second electrode becomes ionised to form a plasma. The plasma has a relatively small potential fall along its length and is at an electric potential much closer to that of the second electrode than to that of the first electrode. A cathode fall region, or plasma sheath, is created around the objects enclosed within the first electrode, accelerating ions onto the surface of the objects. This bombardment ceases after a short time because of the positive surface charge that develops on the objects from the impinging ions. The applied potential is then removed, allowing the process to be repeated in subsequent pulses (unipolar operation). A counter-potential may in some instances be applied to assist in the removal of the positive surface charge before the next pulse is applied (bipolar operation).

In some embodiments, the object or objects to be treated are porous and located relative to the first electrode so as to act as an insulator or dielectric, that acts as a barrier to the continuous transport of charge between the electrodes. In some embodiments the object or objects to be treated are located so that the mutual capacitance between the first electrode and the object or objects to be treated is sufficiently larger than the mutual capacitance between the second electrode and the object or objects to be treated so as to impart a sufficient (negative) potential to the surfaces of the object or objects to be treated.

This method may be used to treat porous objects, including to treat the inside surfaces of pores of a porous object. As well, powders, polymer nanoparticles and polymer-coated magnetic particles may be treated, e.g. for covalent binding of oligonucleotides (DNA or RNA sequences) to the surfaces of the powder or nanoparticles.

The method may provide a way of activating the surfaces in a wide variety of 3D network structures for biosensing or enzymatic processing so as to increase the interaction area relative to 2D detection regions or the surface of solid objects. The plasma activation enables covalent immobilisation a range of species including functional enzymes or biological detection agents, such as antibodies, peptides, RNA sequences, DNA sequences and oligonucleotide sequences, directly from solution onto all surfaces of the 3D networks so modified.

The method may facilitate simple one step dry surface activation of the internal spaces in 3D structures with a wide range of cavity sizes and connectivities.

In some embodiments the method utilises a close-fitting confining sleeve around the structure with inlet and outlet ports to allow effective perfusion of gas throughout the structure. Electrodes forming part of, or being placed around, the sleeve are used to create a plasma discharge in the gas throughout the structure.

In some embodiments the electrodes are powered and grounded electrodes disposed around the sleeve to optimise plasma generation throughout the structure.

In some embodiments the pressure of the gas in the internal spaces is regulated by controlling the flow rate, for example at the inlets and/or at the outlets. The flow rate may be controlled by controlling a pumping speed. The inlet and/or outlet tubes' dimensions and structure are chosen so as to provide the pressure range required for breakdown of the gas within the porous structure to be modified at a flow rate sufficient to replenish the gas species as they are consumed.

The method involves exposing the pores of a porous material to a plasma. This may be achieved by generating a plasma in a static gas within the pores, or it may be achieved by generating a plasma in a gas stream as it passes through the pores. In practice, a certain amount of ionisation may occur before the gas enters the pores, resulting in some plasma entering the pores with the gas.

In the context of this specification, a plasma is considered to be a partially ionised gas, i.e. a gas in which some of the molecules are ionised. These ions are sufficiently energetic to react with the surface of a substrate and/or disrupt the structure of the material at and near the surface of the substrate, through ion implantation into the surface of the substrate. These processes generate reactive sites, for example functional groups or sites with surface embedded radicals (containing unpaired electrons) which can react with molecules and macromolecules such as biological molecules. They may also react with oxygen to generate oxygenated functional groups such as alcohols, carboxylic acids etc. The resulting functional groups may be reacted with a suitable reagent, e.g. a functional molecule, in order to attach a further functional molecule to the substrate. This attachment may be a covalent attachment. Suitable functional molecules include biomolecules, optionally suitably activated (e.g. by attachment of maleimide or other reactive groups). The biomolecule may be an enzyme, a protein, an antibody, an antibody fragment, a peptide, a saccharide, a nucleotide, an oligonucleotide or fragment thereof or some other suitable biomolecule. Additionally, species such as whole cells, cell fragments, micelles, liposomes, hydrogels, labelling molecules, polymer particles or metal particles or polymer coated metal particles may be attached to the porous material. The reactive sites generated by reaction of the porous material with the plasma may be reacted directly with a functional molecule or species to couple said species to the porous material.

Thus following the initial plasma treatment which generates reactive sites (e.g. radical, carbene, ionic etc.) the porous material may be subjected to an oxygen containing gas, e.g. air, water vapour, so as to generate oxygen functionality by reaction of oxygen containing groups with the reactive sites. The resulting functionalised porous material may be reacted with suitable functionalising reagents e.g. biomolecules, by conventional wet chemistry methods. Alternatively, the activated porous material obtained by plasma treatment may be reacted directly with a functional species, e.g. by exposure of the activated material to a solution or dispersion of the functional species, optionally using a bulk solution or dispersion or a nebulised solution or dispersion.

The method may be used to functionalise the surfaces of a porous material. Conventional wet chemical methods may rely on the presence of functionality on the substrate and may therefore be limited in scope. Additionally, for relatively unreactive substrates, harsh chemicals may be necessary for functionalisation. These are commonly hazardous and can cause unwanted side reactions, e.g. chain cleavage of polymeric substrates.

The porous material may have predominantly connected pores, i.e. it will have only a small proportion, if any, of closed pores. This enables the gas to flow through the pores so as to enable surface functionalisation. It will be understood that if closed pores are present, these would not be accessible to a reagent for subsequent attachment of a functional molecule.

The pores may be of any suitable size, e.g. from about 0.1 to 5000 microns in mean diameter. For larger pores, this may be measured by optical microscopy. For smaller pores it may be measured by gas adsorption methods (BET), liquid penetration (e.g. mercury penetration) or other known methods. The pores of the porous material may have a mean diameter of about 0.1 to about 5000 micrometres, or about 0.1 to 2000, 0.1 to 1000, 0.1 to 50, 0.1 to 20, 0.1 to 10, 0.1 to 5, 0.1 to 1, 1 to 2000, 2 to 2000, 10 to 2000, 100 to 2000, 500 to 2000, 1000 to 2000, 1000 to 5000, 10 to 1000, 10 to 100, 100 to 1000 or 50 to 500 micrometres, e.g. about 0.1, 0.2, 0.3, 0.4, 0.5, 1, 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, 1000, 1100, 1200, 1300, 1400, 1500, 1600, 1700, 1800, 1900 or 2000 microns. The minimum diameter of pores to be treated by the present method may be about 0.1 to about 1000 micrometres, or about 0.1 to about 100, 0.1 to 10, 0.1 to 1, 1 to 1000, 10 to 1000, 100 to 1000, 10 to 500, 10 to 100, 100 to 500 or 50 to 500 micrometres, e.g. about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900 or 1000 microns. The porous material may be microporous, mesoporous, macroporous or may have pores in any two or all of these ranges.

In some embodiments the porous material may comprise, or may consist of, particles. The particles may be microparticles or may be nanoparticles or may be macroparticles. The particles may be monodispersed or may have a narrow size distribution or may have a broad size distribution. They may have a mean, or maximum, or minimum, particle diameter of from about 10 nm to 1 mm, or about 10 nm to 100 microns, 10 nm to 10 microns, 10 nm to 1 micron, 10 to 100 nm, 100 nm to 1 mm, 1 micron to 1 mm, 10 microns to 1 mm, 100 microns to 1 mm, 100 nm to 100 microns, 1 to 100 microns or 100 nm to 1 micron, e.g. about 10, 20, 30, 40, 50, 60, 70, 80 or 90 nm, or about 1, 2, 3, 4, 5, 6, 7, 8, 9, 10, 15, 20, 250, 30, 35, 40, 45, 50, 60, 70, 80, 90, 100, 150, 200, 250, 300, 350, 400, 450, 500, 600, 700, 800, 900 or 1000 microns.

The porous material may be electrically non-conducting. The porous material may comprise at least about 20% carbon on a weight or molar basis, or at least about 25% or at least about 30%. In the event that the porous material contains less than about 20% on a weight or a molar basis, the gas provided to the porous material may comprise a carbon-containing compound so as to enable the deposition of an activated coating. The porous material may be polymeric. The polymer may be any desirable polymer. It may be a polyolefin or a polyester or a polyamide or an acrylic polymer or a polyether or a polystyrene or a polyhaloalkene or some other type of polymer. It may be a polymer blend. It may be a homopolymer or may be a copolymer. Suitable polymeric materials for use in the invention include for example polyethylene, polystyrene, polycaprolactone, polysulfone, polypropylene, polytetrafluoroethylene, polychlorotrifluoroethylene, polyurethane, nylon, polyethylene terephthalate, polyamide, polylactide, polyimide, polyacrylonitrile, polyethersulfone, polyetheretherketone, polyarylether ketone, polyetherketone, polyetherketoneketone, polyetherketoneether, polyvinylacetate, polyvinylpyrrolidone polyvinylchloride, polyvinyl alcohol, polymethylmethacrylate, polyacrylamide, polycyanocryate, as well as co-polymers and blends thereof etc. Other suitable porous materials include ceramics, zeolites, sintered metals, sintered metal oxides (e.g. silica, alumina, zirconia, titania etc.) and mixtures of such materials.

The gas flowing into and/or through the porous material in the present method may be, or may comprise, nitrogen, or may be, or may comprise, some other ionisable gas, or may be a mixture of gases, e.g. a mixture of nitrogen with some other gas. The gas may comprise acetylene, ethylene, benzene or some other alkene, alkyne or aromatic compound. It may be a gas containing no oxygen, or containing less than about 100 ppm oxygen (by volume), or less than about 50, 10, 5, 2 or 1 ppm oxygen. The gas may be a vapour such as water vapour or ethanol or methanol or other alcohol. The gas may contain hydrogen. This may assist in the surface modification process. It may include non-reactive gases such as helium, neon, argon. It may comprise reactive gases, such as acetylene, methane, octadiene, n-hexane and allylamine, that are capable of reacting with the surface and form a coating on the inner surfaces of the pores in the porous structure. It may include reactive gases that contain specific functional groups, such as ammonia (amines), water vapour (hydroxyl), heptylamine (amine), acetic acid (carboxyl) and acrylic acid (carboxyl), that are desired to remain covalently coupled to the surface or in the surface coating.

The gas flow rate may be set so as to maintain pressures within the porous structure that are sufficient to achieve breakdown forming a plasma with voltages within the range of the power supply by continually replacing the depleted species. For porous structures with total volume of the accessible pores in the range 0.1 ml to 1000 ml, the flow rate of the gas during ionisation may be between zero and 100 sccm (standard cubic centimetres per minute). Suitable flow rates include zero and from about 10 to 50, 10 to 20, 20 to 100, 50 to 100 20 to 50 or 30 to 70 sccm, e.g. about 10, 15, 20, 25, 30, 35, 40, 45, 50, 55, 60, 65, 70, 75, 80, 85, 90, 95 or 100 sccm. It will be understood that the flow rate will depend in part on the pore size and porosity of the porous material, on the dimensions of the porous material and on the desired functional density for the product. Thus for smaller pore sizes and lower porosities it may be difficult to achieve high flow rate. Also, for a larger amount of porous material, with large total surface area to be modified, a higher flow rate will be appropriate, all other factors being equal. The flow rate should therefore be scaled in proportion to the total accessible pore volume for larger or smaller structures. Finally, the flow rate may be used to affect the density of functionality on the product. This is particularly the case where a low flow rate is limiting the availability of species. In a situation where the flow rate is sufficient to replenish species lost through modification of the surfaces the density may be increased by increasing treatment time, pulse frequency and potentially applied voltage and pressure in the structure. The flow rate of the gas may be sufficient to replenish the gas molecules as they are depleted by reaction to functionalise the porous material. The dimensions and structure (e.g. internal baffles etc.) of the inlet tube may be selected so as to provide a suitable flow rate of the gas. In some instances the gas is not flowed through the porous material during generation of the plasma. Thus the gas may be flowed into the pores and then a pulsed electric field applied so as to generate a plasma in the pores. In a further variation of this, the electric field may then be turned off, further gas allowed to flow into the pores to replace gas depleted by reaction and then the pulsed electric field reapplied so as to generate a plasma in the pores. Such cycles of gas flow-pulsed electric field may be repeated several times, e.g. 1, 2, 3, 4, 5, 6, 7, 8, 9, 10 or more than 10 times. The density of functionality may also be varied by varying pulse voltage, pulse frequency, pressure in the structure and total treatment time.

The pressure of the gas in the pores may be sufficient to support a plasma created by electric fields that can be achieved by the power supply. It may be for example less than about 20 Torr. 1 mTorr is approximately 0.13 Pa. The pressure may be less than about 1, 0.1, 0.01 or 0.001 mTorr, or may be from about 0.001 to 5 mTorr, or from about 0.001 to 1, 0.001 to 0.1, 0.001 to 0.01, 0.01 to 5, 0.1 to 5, 1 to 5, 0.01 to 0.1, 0.01 to 1 or 0.005 to 0.05 mTorr, e.g. about 0.001, 0.005, 0.01, 0.05, 0.1, 0.5, 1, 2, 3, 4 or 5 mTorr. The above pressures are absolute pressures. It can be difficult to measure the pressure within the pores of a porous material. The above pressures may therefore apply to a region downstream of the porous material, or in a containment vessel, e.g. a vacuum chamber, in which the porous material is disposed.

The mean pressure within the material during the gas ionisation may be given by the formula $P=k/d$, where P is the mean pressure, k has a value between about $10^{-5}$ and about $10^{-1}$ in units of Torr·m and d is the diameter of the smallest pore to be functionalised using the method. An optimum or suitable value of k, is that where the voltage needed to breakdown the gas to create a plasma, is a minimum. As Pd moves away from this value in either direction, higher and higher voltages are required to breakdown the gas as per Paschen's law. There are a number of effects that can act to reduce the breakdown voltage required compared to that predicted as discussed previously. By way of example, for a mean pore size of about 4 mm internal diameter, the pressure of the gas, e.g. nitrogen gas, may be in the range 50 mTorr to 1000 mTorr, for example 500 mTorr. With this arrangement 40 microsecond long pulses at 10 kV at 500 Hz over 30 minutes may provide a suitable treatment.

The electric field may be sufficient to at least partially ionise the gas. It may be generated by a potential between two electrodes of at least about 0.5 kV, or of at least about 1, 2, 5, 10, 15, 20, 25, 30, 35, 40, 45 or 50 kV or of about 0.5 to 50 kV, or about 1 to 50, 5 to 50, 10 to 50, 20 to 50, 0.5 to 30, 0.5 to 10, 0.5 to 50, 1 to 20, 1 to 10, 1 to 5, 5 to 30, 5 to 20, 3 to 5 or 5 to 10 kV, e.g. about 0.5, 1, 1.5, 2, 2.5, 3, 4, 5, 6, 7, 8, 9, 10, 15, 20, 25, 30, 35, 40, 45 or 50 kV. The potential may be between a first electrode and a second, optionally earthed, electrode which is biased positively relative to the first electrode. The first electrode may therefore be biased to at least −0.5 kV or at least about −0.5, −1, −1.5, −2, −2.5, −3, −4, −5, −6, −7, −8, −9, −10, −15, −20, −25, −30, −35, −40, −45 or −50 kV relative to the second electrode. In this context it will be recognised that "at least −3 kV" refers to a potential which is negative and has an absolute magnitude of at least 3 kV.

In some embodiments the electric field, and hence the bias, is pulsed. The pulses may have a frequency of about 10 to about 20000 Hz, or about 10 to 10000, 10 to 5000, 10 to 1000, 10 to 500, 20 to 100, 10 to 50, 10 to 20, 20 to 100, 50 to 100, 100 to 20000, 1000 to 20000, 2000 to 20000, 5000 to 20000, 10000 to 20000, 100, to 1000, 500 to 5000, 1000 to 10000, 50 to 500 or 30 to 70 Hz, e.g. about 10, 20, 30, 40, 50, 60, 70, 80, 90, 100, 200, 300, 400, 500, 600, 700, 800, 900, 1000, 2000, 5000, 10000 15000 or 20000 Hz. The individual pulses may have a duration of about 10 to about 200 microseconds, or about 10 to 100, 10 to 50, 10 to 20, 20 to 100, 50 to 100, 100 to 200, 50 to 150 or 30 to 70 microseconds, e.g. about 10, 20, 30, 40, 50, 60, 70, 80, 90, 100, 120, 140, 160, 180 or 200 microseconds. Process time may be significantly reduced at higher frequencies. The upper frequency limit is determined by the capability of the power supply, the maximum gas flow rate (as high flow rates are required to maintain pressure if the depletion rate of species is increased) and the tolerance of the porous material to heating. In some instances, the bias of the electrodes may be reversed for some pulses, i.e. some pulses may be such that the first electrode is negatively biased relative to the second electrode and other pulses may be such that the first electrode is positively biased relative to the second electrode. This may for example represent an alternating bias such that each successive pulse has an opposite bias to the previous pulse. The benefit of alternating the bias of the first electrode relative to the second electrode is that it may assist in the neutralization of any charge on the surface that arises from the bombardment of the surface by ions or electrons of the plasma.

The second electrode is disposed such that an electric field is generated in the gas whilst the gas is in the porous material. The second electrode may for example be on or near or a part of a containment vessel within which the porous material is located and which maintains the required gas pressure. Alternatively or additionally the second electrode may be within the porous material itself. It may be attached to or near an inlet tube which conveys the gas to the porous material.

In some embodiments, the gas that flows into the porous material is selected or controlled to be at a rate that is at least high enough to replenish gas molecules lost in the treatment of the pore surfaces. The method may involve providing gas flow substantially across all of the porous material. Alternatively, the method may involve providing gas to parts of the porous material for treatment and not to other parts of the porous material, or at least to provide gas only a lesser extent that impacts of the level of treatment in the other portions. By passing the gas into only portions of the porous material, and/or by passing the gas at different amounts to different portions, or by covering parts of the porous material with a close fitting mask impervious or relatively impervious to ions with some open or relatively open sections, a pattern of functionality on the porous material may be provided, e.g. regions of functionality and regions of reduced or no functionality.

Ionised molecules of the gas pass into and/or are formed in the pores of the porous material. This may be achieved by means of an electrode (or sleeve) which tightly surrounds the porous material, e.g. surrounds it with a gap between the electrode (or sleeve) and the porous material of no more than about 5 mm, or no more than 2, 1, 0.5, 0.2 or 0.1 mm. In some embodiments, the porous material is located within a sleeve or tube having an inlet coupled to a gas inlet tube so that the gas passes through the sleeve and therefore through the tube. The negatively biased first electrode may be located within, or around or near the sleeve, or may form part of the sleeve or may form the entire sleeve. The porous material may be located within the sleeve with sufficiently little free space that the incoming gas passes into, optionally through, the porous material.

Reaction of the plasma with the porous material generates reactive sites on the pore surfaces of the porous material. These reactive sites may be functional groups in their own right, or may be sites that can react with oxygen or another gas in order to provide functional groups. The initially formed reactive sites may for example be carbene sites, radical sites or some other form of reactive site. In the case of radical sites they are often embedded under the plasma activated surface, to depths of tens of nanometers, and can migrate to the surface to take part in reaction with molecules and macromolecules brought into contact with the surface. In situations where the gas flow within the pores is a transition or molecular flow (as defined by Knudsen number of greater than 0.1) or where the plasma sheath at the surface is thin compared to the mean free path in the gas, there will be few collisions between the ions that have gained energy in the electric field and the background gas atoms, and therefore the ionized species are likely to have enough energy to penetrate beneath the surface, breaking bonds in the sub-surface regions and creating buried radicals which can eventually diffuse to the surface. Radicals and/or other reactive groups may react on exposure to oxygen to form oxygenated functional groups or may react directly with a functional species. Suitable functional groups generated on exposure to oxygen may include peroxides, hydroperoxides, hydroxides, carboxylic acid, carbonyls (e.g. aldehydes) etc. Alternatively, the reactive sites may be reacted with some other reactive material (e.g. reactive gas) to form other functional groups. These may for example be carbon dioxide, acrylic acid resulting in carboxyl groups for example; ammonia, allylamine, heptylamine etc resulting in amine groups for example; and sulfur containing gases to form sulfur containing reactive groups. In the present context, the pore "surface" includes a region adjacent the actual surface, e.g. to a depth or up to about 50 nm from the actual surface, or up to about 45, 40, 35 or 10 nm. It is known that reactive sites at such depths may be quite persistent. They may for example last for over 1 hour, or over 12, 18 or 24 hours or up to 2 years and retain their reactivity or some part of their activity for such periods.

Reaction of the plasma exposed porous material with oxygen or other reactive gas may for example result from merely removing the porous material from its enclosure and exposing it to air, or it may comprise flushing the enclosure with a reactive gas or it may comprise passing the reactive fluid, e.g. liquid or gas, through the inlet tube and through the porous material. In the present context, the term "reactive fluid" indicates that some component of the fluid is reactive towards the reactive sites initially formed on the porous material. That component may be anywhere up to 100% of the reactive fluid, but may be as low as 0.1% thereof. It may be from 0.1 to 100%, or 0.1 to 50, 0.1 to 10, 0.1 to 1, 1 to 100, 10 to 100, 50 to 100, 1 to 50, 1 to 20, 1 to 10 or 10 to 50%, e.g. about 0.1, 0.5, 1, 5, 10, 20, 30, 40, 50, 60, 70, 80, 90 or 100%, by weight or by volume. The remainder of the reactive fluid may be inert towards the initially formed reactive sites or it may also be reactive, so as to generate different reactive groups on the pore surface. Alternatively, the reactive sites may react with the reactive constituent of the gas mixture used in the plasma modification (e.g. in the case of reactive gas) to form a well-adhered film or coating on the surfaces, itself containing functional groups of interest and/or providing desirable surface properties.

Following formation of functional groups on the pore surfaces, these may be used to attach desired molecules onto those surfaces. This may be achieved by conventional wet chemistry taking advantage of the reactivity of the functional groups. In some instances it may be necessary to activate the molecule to be attached so as to enable it to form an attachment, commonly a covalent attachment. Alternatively or additionally, the functional groups may be activated in order to enable attachment. Suitable attachment chemistries, including the range of "click" chemistries and other chemistries for attaching molecules to surfaces, may be used and are well known. These will depend on the nature of the molecule to be attached. Commonly the molecule to be attached will be a biomolecule, e.g. an enzyme, a protein, a saccharide, an antibody fragment or some other suitable biomolecule. Other molecules that may be attached include catalytic molecules or complexes comprising catalytic moieties or ligands which can subsequently converted to catalytic moieties. Commonly the process of attachment will comprise the step of flowing a solution or dispersion of the species to be attached, optionally an activated form of such a molecule, through the porous material. This attachment may follow the plasma treatment, relying on the radical sites for direct covalent attachment or it may take place via an additional chemical linker molecule after formation of suitable functional groups on the surface of the pores as described above. In some instances the flowing may comprise recycling the solution through the pores, and may additionally or alternatively comprise washing the porous material (e.g. by flowing a washing liquid, optionally the solvent from the solution but without the molecule to be attached) after the attachment is completed. Alternatively the process of attachment may comprise exposing the activated porous material to a nebulised liquid comprising the species to be attached. The attachment may be conducted at room temperature or may be conducted at elevated temperature. The suitable temperature may depend on the nature of the attachment reaction, the nature of the porous material, the nature of the species to be attached etc. For example, elevated temperatures may be inappropriate for temperature sensitive species.

The porous material may be any substrate to which attachment of particular species, e.g. biomolecules, is required. It may be for example a scaffold for tissue engineering such as a scaffold for encouraging the ingrowth of bone from surrounding tissue for the repair of part of the skeleton after injury or surgery. It may be a stent. It may be a prosthetic device. It may be a device for flow chemistry. It may be a packing for chromatographic purposes. It may be a 3D membrane structure used as a filter or part of a sensor. It may be a support for enzymes used in food, chemical or biofuel manufacture. It may be a 3D cell culture platform used to better represent biological phenomena that occur in vivo.

The disclosure also includes an apparatus for plasma ion processing of a porous material, for example for functionalising the porous material. Particular components of this apparatus are set out below.

The apparatus includes at least a first electrode and a second electrode. The electrodes are configured for providing an electric field, for example a pulsed electric field, which generates ions in the gas so as to generate a plasma. These ions interact with the pore surfaces of the porous material through ion implantation and/or chemical reactions to generate reactive sites and/or functional groups. Each of the electrodes may be a single electrode or may be a multiple electrode. For example the first electrode, which is negatively biased in the surface modification phase of operation, may be a single sleeve electrode surrounding the porous material to be treated. Alternatively it may comprise a number of electrodes (e.g. 2, 3, 4, 5 or more than 5) surrounding a sleeve which in turn surrounds the porous material. Where there are a plurality of electrodes, they may be independently or collectively controlled. If collectively controlled, the plurality of electrodes may be connected by a substantially zero or low resistance path.

In some embodiments the first electrode is an annular electrode or a cylindrical electrode. The second electrode, which in many embodiments is an earthed electrode, may comprise a single electrode disposed on a containment vessel. Alternatively it may comprise multiple electrodes disposed on the containment vessel, or may comprise one or more electrodes on the containment vessel and an electrode disposed near or within the porous material (or within the sleeve in which the porous material is located in use). The skilled person will readily appreciate that a variety of such options is available for each electrode. An important aspect of the location of the electrodes is that they are disposed so that when a potential is applied between them, the resulting electric field is sufficiently strong in the porous material to at least partially ionise gas therein so as to generate a plasma.

The apparatus includes a power supply or a connection suitable for receiving power from a power supply. The power supply or power supply connection is coupled to the first electrode and/or the second electrode and, in use, provides a negative bias to the first electrode relative to the second electrode during the surface modification phase of the process. It may on occasion also provide a positive bias relative to the second electrode. Providing a positive bias may assist in neutralizing any charge building up during the surface modification process. Alternatively positive pulses if required may be provided by a separate synchronized power supply. The negative bias relative to the second electrode is pulsed to give rise to a pulsed electric field, as described above. The power supply may be capable of providing a pulsed bias of a frequency and intensity as described earlier. It should be of sufficient strength to provide an electric field of sufficient strength to ionise said gas to generate a plasma. The actual power may vary depending on the location of the first and second electrodes, on the nature and pressure of the gas and on the level of ionisation required.

The apparatus includes a support for holding the porous material in use in such a way that gas from a gas inlet is constrained to pass at least into or through, the porous material, and in particular into or through, pores thereof. The support may be in the form of a tube or sleeve having an internal cavity in which the porous material is located. In some embodiments, when the porous material is in the support, a substantial portion of the gas or substantially all of the gas provided at the gas inlet is constrained to pass through the porous material. In this instance, there may be a significant pressure drop across the porous material. In some embodiments the porous material may not completely fill or block the passage of gas through the support. In this instance, some gas may pass by the porous material in use and gas may enter the pores simply by diffusion. In such instances, the pressure drop may be much less, and may be very low or negligible.

As discussed above, a gas inlet is coupled to the support such that a gas passing through the inlet passes into pores of the porous material. The gas inlet may include an inlet tube. The coupling of the inlet tube to the support may be substantially gas tight, so that all gas passing through the inlet tube passes into the support and to the porous material. The inlet tube may be constructed of any suitable material that is capable of withstanding the generated electric field and the ionised gas generated by it. A suitable material is polyurethane.

In some embodiments the apparatus further includes a containment vessel. The support, first electrode and porous material are disposed within the containment vessel, which is configured to allow a vacuum to be applied. In some embodiments the support and containment vessel are integrally formed. A containment vessel configured to operate as a vacuum chamber may be beneficial in preventing parasitic discharges and leaks from atmosphere that would interfere with the treatment process in cases whether the support and/or the connections to the support are not hermetic. In this instance, the inlet tube may pass through the vacuum chamber. It may be sealed to the chamber in an airtight manner. The dimensions and design of the inlet tube can be utilized to optimize the pressure/flow rate combination to achieve gas breakdown throughout the porous structure at a flow rate capable of adequately replenishing species consumed in the process. Tuning the dimensions and design of the inlet tubing facilitates tuning the pressure in the porous structure for a given flow rate by varying the impedance to flow presented by the inlet tubing. A similar strategy can be applied to a gas outlet, including for example outlet tubing if the pressure/flow rate combination at the downstream side of the porous structure is to be tuned. The containment vessel may be an openable vessel in order to allow the porous material to be inserted and removed. The containment vessel may in some instances have a second gas inlet to allow a second gas to be fed into the inside region. This may be of use in cases where reactive sites generated on the porous material are to be reacted with a gas other than air or in cases where a film or coating is to be deposited on the surfaces.

The apparatus includes a gas supply or a connection for a gas supply. The gas supply or connection is configured to supply an ionisable gas to the gas inlet. If a containment vessel is present, the gas supply is commonly located outside the containment vessel. The gas supply may comprise, for example a cylinder containing the relevant gas. It may also comprise a regulator for controlling the flow of the gas into the inlet tube. As noted earlier, a suitable gas is nitrogen or a gas containing nitrogen, however other ionisable gases or mixtures thereof may at times be used.

In some embodiments the apparatus includes a pump for facilitating the provision of the ionisable gas to the porous material. For example, a pump may provide a partial vacuum in and/or downstream of the support. In this context, the term "downstream" applies to that region into which the gas flows after passing through the porous material. In the event that a containment vessel is present, the pump may be coupled to the containment vessel so as to apply a partial vacuum to the region inside the containment vessel. In some embodiments there may be no containment vessel. In such cases, one option is to couple the pump to a gas exit manifold which is itself coupled to the support so as to constrain gas passing from the support through the porous material to pass through the gas exit manifold. In such embodiments, the gas exit manifold may be detachable from the support so as to allow the porous material to be inserted into and removed from the support.

In some embodiments the gas inlet also operates as a gas outlet. In these embodiments the chamber may be closed off from gas inlets or outlets to avoid the entrainment of powder in the gas. The gas may be supplied in the first filling of the porous structure and replenished after a time of operation as necessary.

The inventors have demonstrated that porous interconnected 3D printed PEEK structures after treatment as described herein encourage more growth of Saos-2 cells into the structure, when incubated in solution with the cells than untreated scaffolds. Saos-2 cells are a type of human bone cell. The inventors have also demonstrated that polymeric interconnected porous 3D polycaprolactone (PCL) structures treated as described herein covalently immobilise protein directly from solution. The covalency of the immobilisation was confirmed using FTIR spectroscopy to detect the presence of protein before and after SDS (sodium dodecylsulfate) washing. This demonstrates that the treated structures can be functionalised by covalent linking of molecules from solutions placed in contact with the plasma treated surfaces using approaches such as incubation, painting, spraying or dip-pen spotting. Multiple functionality can be added by sequentially exposing to different solutions or by exposing to a mixed solution. Surface density of functionalisation can be controlled by varying the length of contact time with the functionalising solutions and/or the intensity of the plasma surface treatment. Since solution conditions such as pH and ionic strength do not need to be regulated to achieve covalent immobilisation, they can be tuned to optimise the conformations, orientations and density of immobilised molecules.

In addition to providing a practical route to covalent functionalisation of thermoplastic scaffolds, the plasma activation process described herein also enables effective integration of the structures with extracellular matrix mimicking hydrogels (both synthetic and natural) and self-assembled peptide fibres. Hitherto, creating composite structures of thermoplastic scaffolds and hydrogels as needed to create appropriate mechanical properties has been problematic due to the wettability mismatch. The treatment method of the present disclosure resolves the problem of integrating hydrogels by making the treated scaffolds hydrophillic. The plasma activation also provides covalent attachment sites for beta-peptides that can self-assemble into ECM-like fibres throughout the scaffold.

One application of the disclosed method of treatment is in providing 3D biofunctionalised structures for use in cell assays and cell culture studies, tissue engineering, biosensing and chemical/food/biofuel processing. The method may provide the structures in a relatively practical, environmentally friendly and cost-effective way. Previous solutions for achieving covalently functionalised structures typically utilise wet chemistry to react linker molecules and then to attach the functional motifs. These approaches have many limitations including the difficulty of using wet-chemical methods (i.e. liquid flow) in confined spaces for each stage of the functionalisation. The necessity of using potentially damaging solvents adds cost and imposes requirements for safe disposal which do not exist in our approach. A further major problem with chemical linker approaches for any medical application is the need to establish and prove protocols that ensure that all traces of any potentially harmful substance used in the processing are removed. This may present a road block to regulatory approval. The disclosed method of treatment can be used without applying any solvents to the porous material.

Plasma Ion Activation of Three Dimensional Scaffolds

FIG. 1 shows an example plasma immersion ion implantation set up for treating the surfaces of two-dimensional materials such as sheets or slides. A plasma is generated in the grounded vacuum chamber (not shown), for example by an auxiliary rf electrode (not shown), and a high voltage pulsed bias applied to the sample holder draws ions from the surrounding plasma to be implanted into the surface of the sample.

Figure 2:
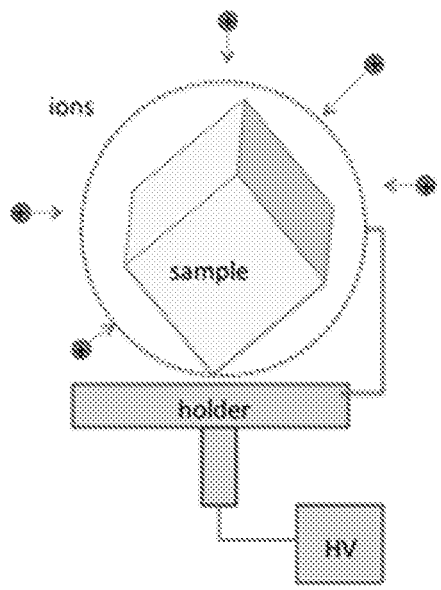
FIG. 2: A diagram illustrating a process for plasma functionalisation of surfaces. Ions accelerated out of a plasma through a mesh biased with 20 kV pulses implant into the surface of the object inside the mesh. The holder is mounted in a grounded vacuum chamber and the positive terminal of the high voltage pulsed power supply (HV) was connected to the second electrode (not shown), which was at ground potential.

This can be extended to the surfaces of three dimensional objects by surrounding the object by a mesh electrode that is electrically connected to the pulsed high voltage supply, for example via a holder connected to the voltage supply (HV) as shown diagrammatically in FIG. 2. In this case the plasma sheath forms around the mesh and accelerates ions through the mesh. These energetic ions then continue towards the sample and implant into its surface. This process is successful for treating surfaces that have a line of sight to the mesh consistent with the directionality of the incoming ions being accelerated through the mesh.

The present disclosure demonstrates the implementation of a process for the modification of the internal surfaces of complex structures with interconnected or otherwise accessible pores (i.e. the structures have porosity).

In general the method includes surrounding the structure with high voltage electrodes and arranging for gas to flow into or through the interconnected regions that require modification. The gas flow is controlled or regulated so as to ensure that sufficient pressure is achieved inside the structure to create a discharge in the inner volumes and to ensure that the gas flow in all regions requiring modification is sufficient to supply the fluence of ionized species required for the modification.

The inventors have found that effective modification of the internal surfaces is achieved by providing a pressure or range of pressures inside the internal surfaces to be modified sufficient to sustain a gas discharge at the voltage applied, so that a plasma can be created throughout the internal void structures. Once this condition is met the treatment fluence received in various locations depends on the supply of ions, which for example depends on the flow of gas species through the void spaces. The internal surfaces of voids that receive greater gas flow also receive a higher degree of modification. This aspect is clearly demonstrated in embodiment 4.

Embodiment 1

Figure 3:
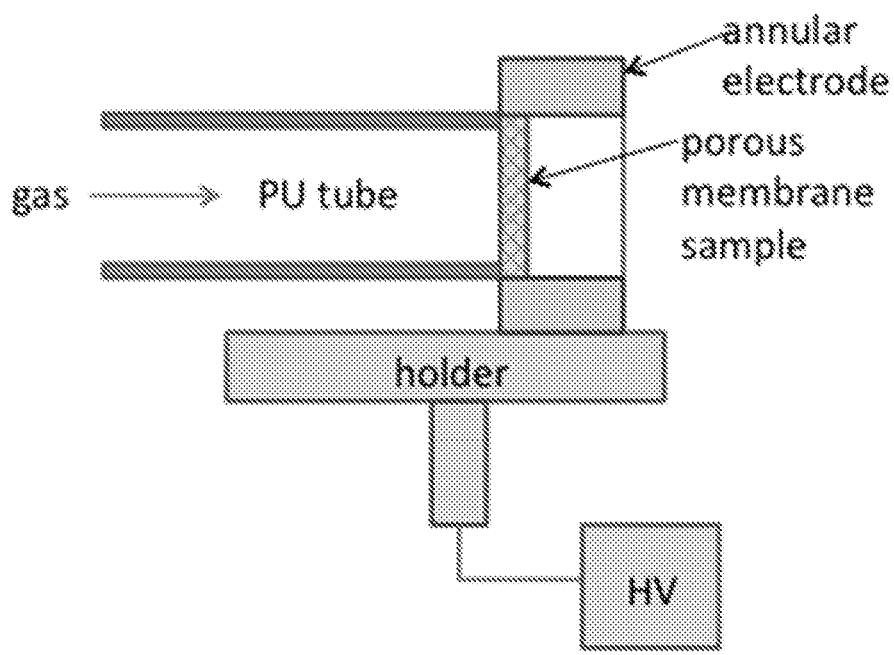
FIG. 3: Schematic diagram of a system used to treat the internal surfaces of a fibrous membrane sample according to Embodiment 1 of the present disclosure. This assembly was placed in a grounded vacuum chamber. The feed-through supplying gas to the PU (polyurethane) tube and into the internal structure of the sample was also grounded. The positive terminal of the high voltage pulsed power supply (HV) was connected to the second electrode (not shown), which was at ground potential.

One embodiment used to treat a fibrous membrane is shown in FIG. 3. FIG. 3 schematically shows a part of an apparatus for treating the membrane.

With reference to FIG. 3, the apparatus comprises a first electrode ("annular electrode") and a second electrode, not shown in FIG. 3. A power supply ("HV") is configured to provide a pulsed potential between the first and second electrodes such that the first electrode is negatively biased. In the embodiment shown in FIG. 3, the first ("annular") electrode serves the function of a support for holding the porous material ("porous membrane sample"). In other embodiments the support and first electrode are not integral. An inlet tube "PU tube") is coupled to the first electrode so that gas provided from a gas supply (not shown) through the PU tube passes through the porous membrane sample. In the embodiment shown in FIG. 3, the PU tube, annular electrode, porous membrane sample and holder are located inside a containment vessel (not shown). The second electrode (not shown) is disposed on that containment vessel and is earthed. A vacuum pump (not shown) is provided to apply a vacuum inside the containment vessel providing the downstream pressure to the structure to be modified. A downstream pressure of the gas may be less than about 5 mTorr.

In operation, an ionisable gas, e.g. nitrogen, is supplied from the gas supply to the porous membrane sample. A vacuum applied within the containment vessel by the pump causes the gas to flow through the pores of the porous membrane sample. A pulsed potential between the first and second electrodes provides a negative bias to the first electrode surrounding the porous membrane sample and generates a pulsed electric field sufficient to cause the gas to ionise. As the partially ionised gas flows into the pores, it reacts with the pore walls to generate reactive species on the surfaces of the walls. Once the containment vessel is opened to the atmosphere after the power supply is turned off, reaction of these reactive species generates functional groups on those walls.

In a particular example then, the entire assembly shown in FIG. 3 is placed in a grounded vacuum chamber evacuated by a turbo pump to a background pressure of around $10^{-6}$ Torr. The polyurethane (PU) tube was connected to a nitrogen gas supply via a mass flow controller and gas was pumped into the system at a flow rate of 70.4 sccm (standard cubic centimetres/second). The PU gas supply tube was fitted tightly into the electrode so that the gas had to flow through the pores of the polycaprolactone (PCL) fibre mesh being treated. The annular electrode connected to the high voltage power supply via the sample holder which was biased to negative 10.2 kV with 20 µs pulses applied at 50 Hz. The pulsed dc bias created a plasma discharge in the PU tube and the fibre mesh. The process was run for 10 minutes and the inlet pressure was measured to be 1.2 Torr while that in the chamber was $2\times10^{-3}$ Torr. The fibre mesh being modified in this example was made of PCL fibres with approximate diameter of 22-30 µm and the pore size was approximately 0.2 mm. Some arcing on the PCL membrane was observed during the treatment process.

Figure 4:
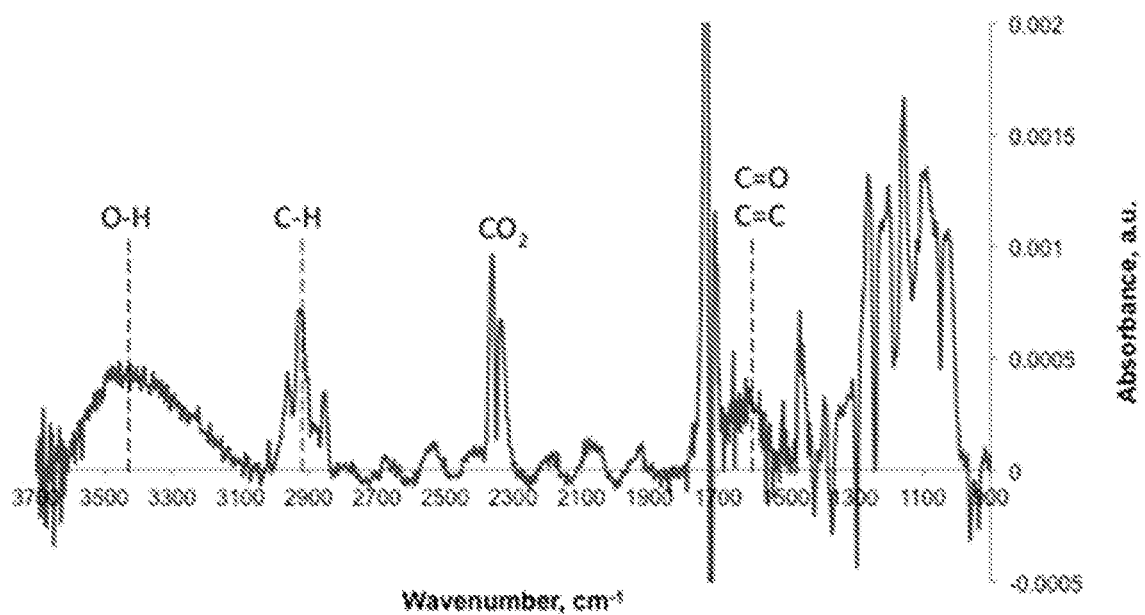
FIG. 4: FTIR (Fourier transform infrared) spectrum taken from the downstream side of the gas flow from the system of FIG. 3, which shows the vibrations associated with new chemical bonds and groups created by plasma surface modification. A reference spectrum taken prior to modification has been subtracted clearly revealing these spectral features typical of surface treatment by energetic ion implantation.

Plasma modification of the surfaces was observed. An FTIR spectrum taken from the surface at down-stream side of the gas flow is shown in FIG. 4. The spectrum of the surface prior to modification has been subtracted clearly showing C═C, C═O and O—H bonds introduced by the surface modification process.

Embodiment 2

Another embodiment (FIG. 5) shows the process applied to a larger PCL scaffold (a porous PCL cylinder).

In this embodiment aluminum foil was wrapped around the cylinder and contacted on one side to the high voltage powered substrate holder. An additional wire electrode was inserted into a sealed PU tube which fitted into the hollow in the PCL cylinder. The other end of the wire was connected to the pulse biased substrate holder. An adapter was used to connect one end of the foil wrapped cylinder to a polyurethane gas inlet tube. The entire assembly was placed into a grounded vacuum chamber pumped by a turbo pump to base pressure of approximately $10^{-6}$ Torr. The second electrode (not shown) was disposed on that containment vessel and is earthed. The flow of nitrogen into the PU tube was regulated at 50.2 sccm with a mass flow controller. A negative bias of 5.5 kV for 20 µs pulses was applied to the holder at 50 Hz. This bias created a plasma discharge in the PU tube and in the fibre mesh hollow cylinder scaffold to be modified. In this example the scaffold was made of PCL fibres with approximate diameter of 0.7 mm and with approximate pore size of 0.9 mm between the fibres.

Figure 6:
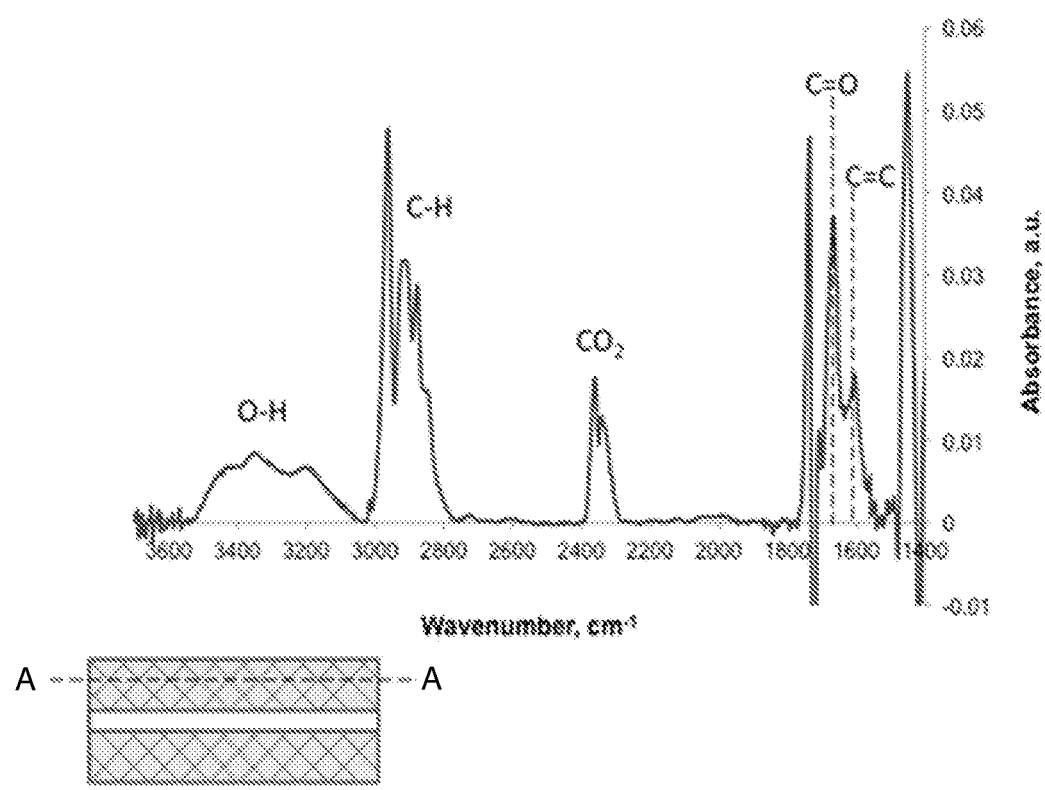
FIG. 6: FTIR spectrum showing the vibrations associated with new chemical bonds and groups created by plasma surface modification using the system of FIG. 5. A reference spectrum taken prior to modification has been subtracted clearly revealing these spectral features typical of surface treatment by energetic ion implantation.

The FTIR spectrum shown in FIG. 6 confirms that the internal surfaces of the structure are treated. The PCL cylinder was sectioned in the location indicated by the dashed line A-A in FIG. 6, to measure the FTIR spectra on the surface of its inner cells. A reference spectrum from an unmodified sample has been subtracted from the spectrum of the treated sample to clearly reveal the spectral features typical of surface treatment by energetic ion implantation.

Embodiment 3

Figure 5:
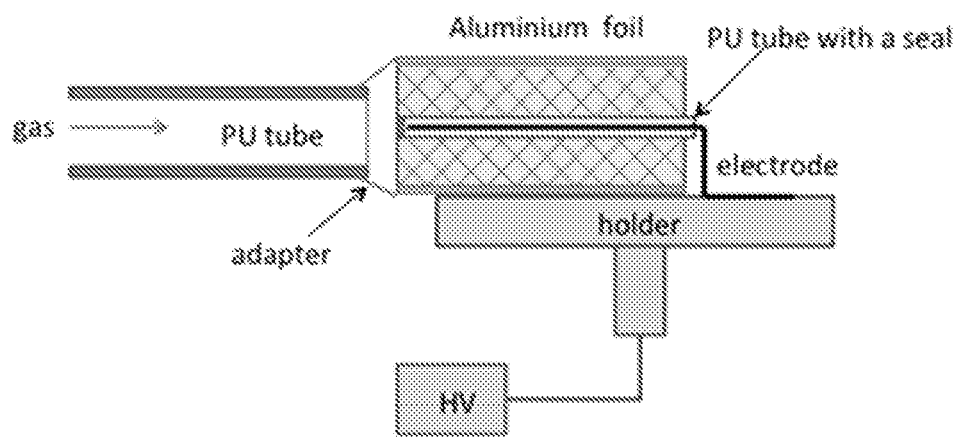
FIG. 5: Schematic diagram of a system used to treat the internal surfaces of a porous hollow cylinder according to Embodiment 2 of the present invention. This assembly was placed in a grounded vacuum chamber. The feed-through supplying gas to the PU (polyurethane) tube and into the internal structure of the sample was also grounded. The positive terminal of the high voltage pulsed power supply (HV) was connected to the second electrode (not shown) which was at ground potential.

In another embodiment, the setup of FIG. 5 was used without the wire electrode, so that the cavity in the PCL cylinder was blocked by the closed PU tube alone. This PU tube insert was therefore not subjected to pulsed bias, rather it served only to prevent gas flow through the large central cavity of the fibre mesh hollow cylinder scaffold. The scaffold modified here was identical to the one modified in Embodiment 2.

The flow of nitrogen into the PU tube was regulated at 54.5 sccm with a mass flow controller. A negative bias of 4.5 kV for 20 µs pulses was applied to the holder at 50 Hz. This bias created a plasma discharge in the PU tube and the fibre mesh hollow cylinder scaffold to be modified. The process was run for 10 min and the inlet pressure was measured to be 1.3 Torr while that in the chamber was $1.2\times10^{-3}$ Torr.

Figure 7:
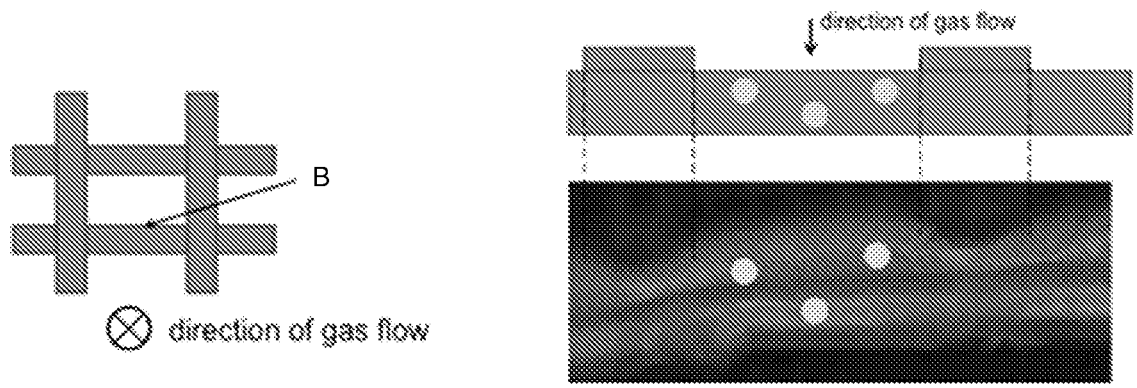
FIG. 7: The left panel is a plan view (looking along the gas flow direction) schematic diagram showing where spectra were measured on a cell taken from the treated porous cylinder according to Embodiment 3 of the present invention. The right panel shows an image of the fibre measured looking normal to the gas flow both schematically (upper) and taken by the FTIR microscope (lower). The circular spots indicate sites at which spectra were measured.
Figure 8:
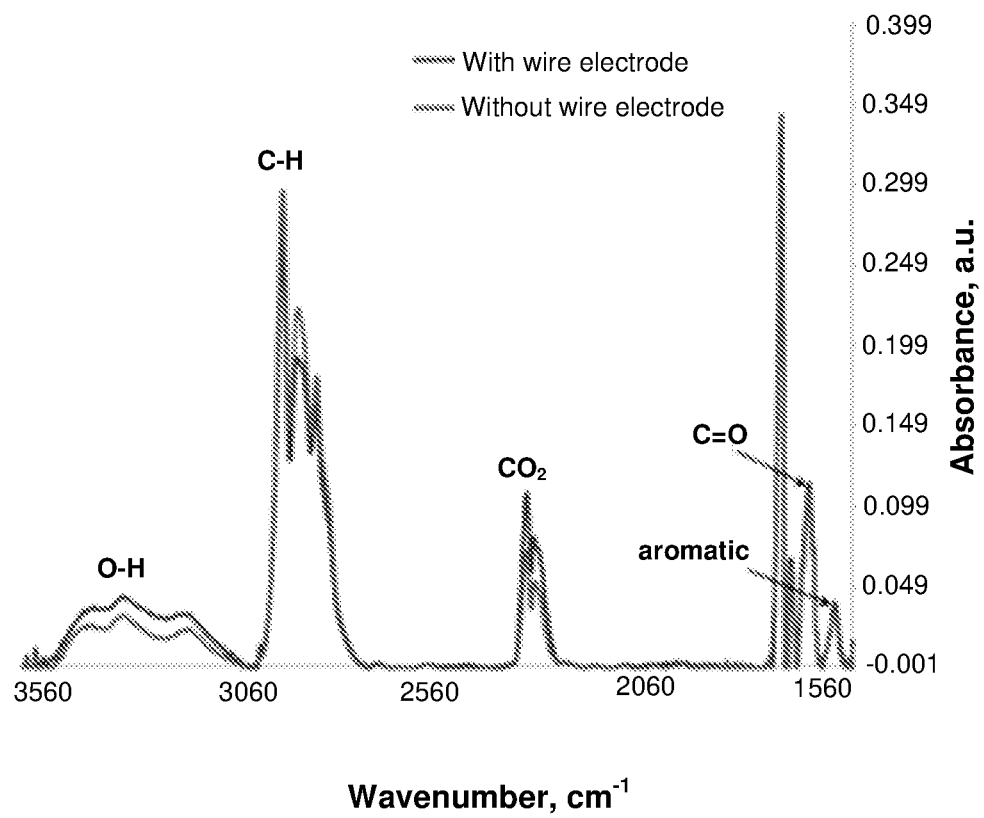
FIG. 8: FTIR spectra showing the vibrations associated with new chemical bonds and groups created by plasma surface modification according to Embodiment 3 of the present invention. A reference spectrum taken prior to modification has been subtracted, clearly revealing the spectral features typical of surface treatment by energetic ion implantation. The spectra were normalized to the intensity of the 1730 cm$^{-1}$ vibration line. The results show that the modification in embodiment 3 (red) is not significantly different from that created by embodiment 2 (blue).

FIG. 7 shows, by reference arrow B in relation to one cell of the PCL cylinder, where FTIR spectra were taken on the internal surfaces of the fibre mesh hollow cylinder scaffold. The FTIR spectrum shown in FIG. 8 confirms that the internal surfaces of the structure were treated as in the case where the wire was present (Embodiment 2).

Embodiment 4

Figure 9:
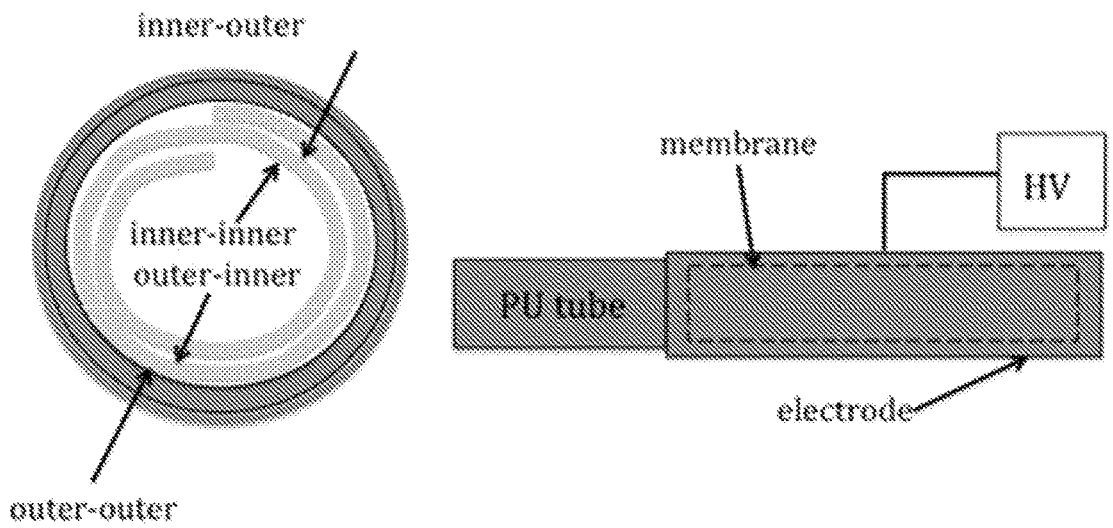
FIG. 9: The left panel shows a schematic diagram of the PU tube with the rolled membrane inserted inside looking into tube according to Embodiment 4 of the present invention. The labels on surfaces indicate the various sites at which FTIR spectra shown in FIG. 10 were taken. The right panel shows a side on view of the PU tube inserted into the hollow cylinder electrode. The dashed lines indicate the position of the rolled membrane. Gas was allowed to flow through the PU tube from left to right to achieve treatment. This assembly was placed in a grounded vacuum chamber. The feed-through supplying gas to the PU tube and into the internal structure of the sample was also grounded. The positive terminal of the high voltage pulsed power supply (HV) was connected to the second electrode (not shown), which was at ground potential.

In another embodiment, the apparatus was configured to provide localised gas flow to affect the fluence of the modification. In this embodiment, a fibrous membrane was rolled and placed inside a polyurethane (PU) tube. The PU tube was then inserted into a hollow cylindrical electrode as shown in FIG. 9. The hollow cylinder electrode was connected to a pulsed high voltage (HV) power supply (also shown in FIG. 9).

The entire assembly was placed in a grounded vacuum chamber evacuated by a turbo pump to a background pressure of around $10^{-6}$ Torr. The polyurethane (PU) tube was connected to a nitrogen gas supply via a mass flow controller and gas was pumped into the system at a flow rate of 50 sccm. The hollow cylinder electrode connected to the high voltage power supply was biased to negative 5.6 kV with 20 µs pulses applied at 50 Hz. This bias created a plasma discharge in the PU tube and the fibrous membrane to be modified. The process was run for 10 min and the inlet pressure was measured to be 1.3 Torr while that in the chamber was $1.1\times10^{-3}$ Torr. The fibre membrane being modified in this example was made of PCL fibres with approximate diameter of 22-30 µm and had approximate pore size of 0.4 mm.

Figure 10:
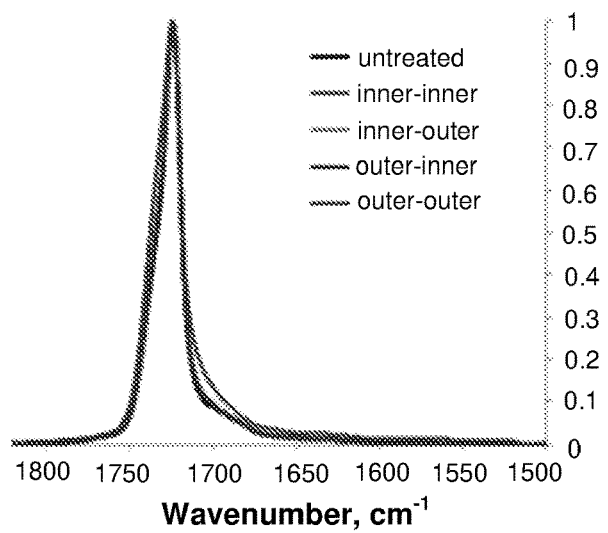
FIG. 10: FTIR spectra (left) taken from the positions labelled in FIG. 9 on the rolled membrane show changes to the absorption of the C=O vibrations due to the plasma surface modification. The histogram (right) shows absorption intensities at 1706 cm$^{-1}$. All positions are treated with the side exposed to the highest volume of gas flow (inner-inner) receiving a significantly higher level of modification.
Figure 10:
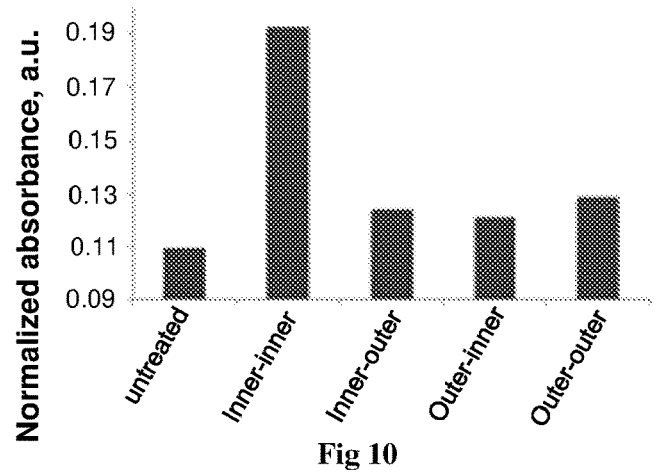

The FTIR spectra taken at the surfaces of the rolled membrane indicated in FIG. 9 are shown in FIG. 10. The spectra confirm that the internal surfaces of the structure are treated. Increases in the absorption of the C═O vibrations are evidence of surface modification. The spectrum taken from the inner most part of the rolled membrane (inner-inner) shows the highest level of modification by far while the other three surfaces which were close to another part of the membrane or the wall of the PU tube show lower levels of modification. The histogram (right) shows the absorption intensities at 1706 cm$^{-1}$ (C═O). All sites are treated with the inner most surface (inner-inner) receiving a significantly higher level of modification than the other three (inner-outer, outer-inner and outer-outer).

It should be noted that the pressure in the structure should be maintained at the values required to achieve modification in the smallest pore sizes. This requires consideration of the pressure drop across the structure. For example if a large channel is present in a structure that contains also small pores, the pressure needs to be set to achieve ionization of the gas in the small pores. Gas will be depleted more rapidly in the smallest pores due to the small volume of available gas hence requiring the flow rate to be set in such a way as to maintain the pressure in a suitable range throughout the modification process. A situation in which the gas supply rate is too low to provide sufficient feedstock for the small pores will be apparent as a lower level of modification intensity in the smaller pores.

Embodiment 5

Figure 11:
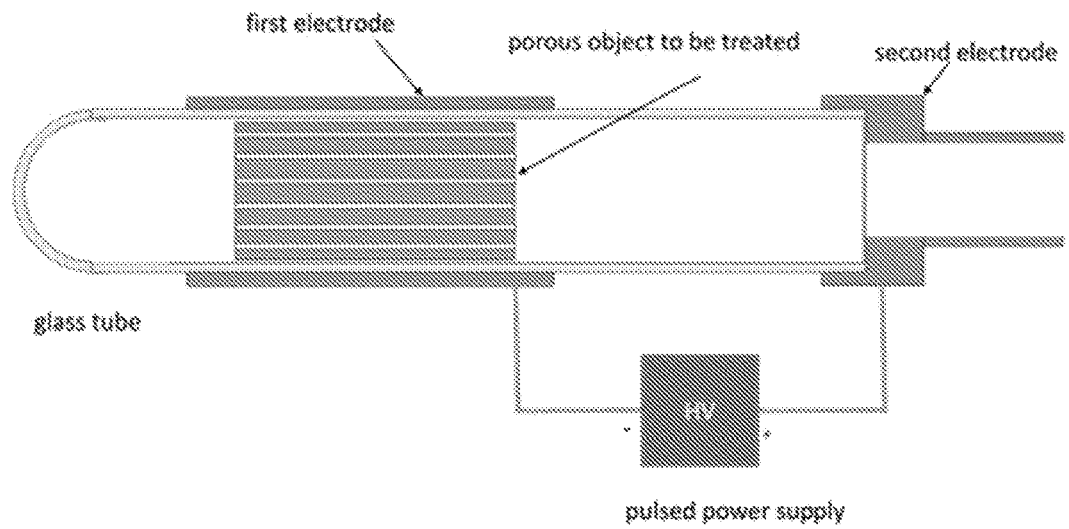
FIG. 11: Schematic diagram of a system according to Embodiment 5 of the present disclosure, used to treat the surfaces of particles and can also be applied to treat the surfaces of a porous material in the form of a scaffold that can be placed inside the tube in the region surrounded by the first electrode. The first electrode is a conductive sleeve surrounding a glass tube closed at one end. The glass tube may act as a support for the porous material placed inside it. The second electrode is a leak-tight fitting attached to the glass tube that connects the glass tube to a grounded bellows through which the gas is admitted into the tube. In the case where the porous material includes or consists of particles, the flexibility of the bellows allows the tube to be vibrated during the treatment so as to separate the particles. A valve on the bellows is closed whilst the tube is vibrating so as to prevent the escape of particles into a vacuum pump. The high voltage pulsed power supply (HV) is connected to the first and second electrodes. In some embodiments the second electrode is at ground potential.
Figure 12:
FIG. 12: The 3D printed PEEK porous scaffolds treated in the apparatus of FIG. 11 are the left two scaffolds shown immersed in the cell culture medium for the growth of Saos-2 cells. The scaffold on the right is untreated and is not easily wettable by the cell culture medium and hence floats in it.

In another embodiment, illustrated in FIG. 11, the porous structure is a porous scaffold or a powder. The treatment is made to activate the internal surfaces of the porous scaffold or external surfaces of the particles of the powder. The porous structure is placed inside a glass tube and the first electrode is a closely fitting conducting cylinder placed around the glass tube. In the case where the porous material includes or consists of particles, the glass tube may be connected to a source of vibration so that its surfaces oscillate and cause the particles that adhere to the walls to be suspended in the gas. The glass tube is connected to a fitting so that the connection is leak-tight and capable of holding a vacuum. The connection is also metallic and is connected to a metallic bellows. The connection and the bellows act as the second electrode and are earthed. The bellows is connected to a chamber fitted with a vacuum gauge and connected to a valve. The valve is connected to a vacuum chamber.

During treatment, the glass tube and reservoir are filled with a mixture of nitrogen and acetylene and the first electrode has negative voltage pulses applied to it. In some embodiments, during treatment vibrations are allowed to move the glass tube, causing the particles (if present) to be suspended in the plasma. A coating from species generated in the plasma from the acetylene forms on the particles, that is itself bombarded by ions.

The plasma is excited by −2 kV pulses from a pulsed power supply. The initial filling gas pressure is typically 10 mTorr.

Applications for the disclosed method include preparation of scaffolds for in vitro cell culture and expansion including growth of complex organs outside the body. For example, in vitro culture systems for improved accuracy testing of the effects of drugs and other stimuli on cells and directed cell differentiation by spatially varied topology and biochemical functionalisation of the scaffold to grow artificial organs. The technology may also be used to provide more biocompatible surfaces for artificial structures used in blood processing and filtering for example. This includes artificial kidneys, livers and lungs.

This technology may also have application to enabling continuous flow enzymatic processes in the areas of chemical, food and biofuels processing.

The nanoparticles created from ionised carbon precursor in a plasma discharge allow direct covalent immobilisation of a variety of molecules by means of radicals contained within the particles. The surface of the nanoparticles, containing unpaired electrons, can be readily and easily functionalised through the immobilization of a variety of biomolecules which include pharmaceutical agents, drug molecules, targeting ligands, peptides, proteins and imaging agents. The immobilization of biomolecules onto the nanoparticle surface according to the present disclosure is or can be a one-step process, achieved by simple incubation without the need for intermediate grafting and passivation steps with organic molecules or other chemical intermediates. This represents a significant process simplification, reduced environmental impact and significant cost reductions in the commercial context. Furthermore, the immobilised biomolecules maintain their bioactivity after being immobilised onto the surface of the nanoparticles. Both bare nanoparticles and biomolecule conjugated nanoparticles are readily internalised by various cell types and do not induce cytotoxicity in cells at all tested concentrations. Additionally, drug-conjugated nanoparticles maintain cytotoxic capacity after internalisation by cancer cells. The covalent immobilization capability of the nanoparticles and the bioactivity of biomolecule conjugated nanoparticles is maintained after long-term freeze-dried storage.

Embodiment 6

In another embodiment a porous scaffold was prepared by 3D printing in ABS plastic. The dimensions of the object were 1 cm diameter and 5 cm long. The object was printed with 3 holes of 2 mm diameter parallel to the axis and located at equal spacings across a major diameter of the cylinder. The object was printed in two halves so that the interior surfaces of the pores could be inspected when the two halves were separated. The object was placed inside a closed glass test tube of 15 mm internal diameter and 200 mm length and the gas was evacuated to a pressure of less than 0.1 mTorr using a vacuum pump consisting of a rotary vane pump and a turbomolecular pump. A copper cylinder close fitting around the outside of the test tube was connected to a pulsed power supply operating at −5 kV with the counter electrode at earth potential being the stainless steel flexible pipe connecting the test tube to the vacuum pump. Nitrogen gas was allowed to fill the test tube to a pressure of 500 mTorr and the test tube was isolated from the vacuum pump. Pulses were applied for a period of 20 minutes at a frequency of 500 Hz and a pulse length of 200 microseconds. Upon completion, the test tube was vented to air and the treated object separated in the two halves to enable inspection of the surfaces of the pores. The surfaces of the pores were found to have been modified to give a brown colouration typical of the effects of plasma immersion ion implantation on ABS polymers.

Embodiment 7

In another embodiment, a porous scaffold of PEEK was prepared by 3D printing in an AON 3D printer where PEEK filaments were heated and deposited onto a build plate to build an object in the form of a series of layers where each layer consists of a set of evenly spaced parallel bars with a mark to space ratio of approximately 1:1. To form the object, subsequent layers were rotated with respect to the layer underneath to form a helical structure. The printed object was approximately 25 mm in diameter and 10 mm high. This gave a structure with void spaces that were connected throughout. The structure was treated by placing it in a conical flask, the base of which was surrounded by a copper foil electrode to a height of approximately 25 mm. The flask was filled with nitrogen plasma to perform a treatment as for the tube of embodiment 5. After treatment, the scaffold was immersed in a cell culture medium containing Saos-2 bone cells. Scaffolds that had not received treatment were used as controls. It was observed that the treated scaffolds immediately sank in the medium and were penetrated by medium, whereas the control scaffolds floated in the medium and had to be held down to become completely wetted by the medium. After incubation of the scaffolds with cells for approximately 2 weeks, the scaffolds were weighed to determine the amount of biomass present in and on the scaffolds. It was found that the treated scaffolds acquired significantly more biomass than the untreated controls.

Embodiment 8

In another embodiment, the inner surfaces of hollow fibres were treated. In particular, a cassette containing a bundle of over 10,000 polyethersulfone (PES) hollow fibre membranes was treated. The membranes were in the form of capillaries with about 30 cm length, 200 μm inner diameter and 50 μm wall thickness. The walls contained pores of 10-50 nm diameter. The fibres were embedded at both ends in resin so that the volumes inside of the fibres were connected to the inlet and outlet ports on the axis of the cassette, whilst the volume outside surfaces was connected to two ports on the side of the cassette.

Figure 13:
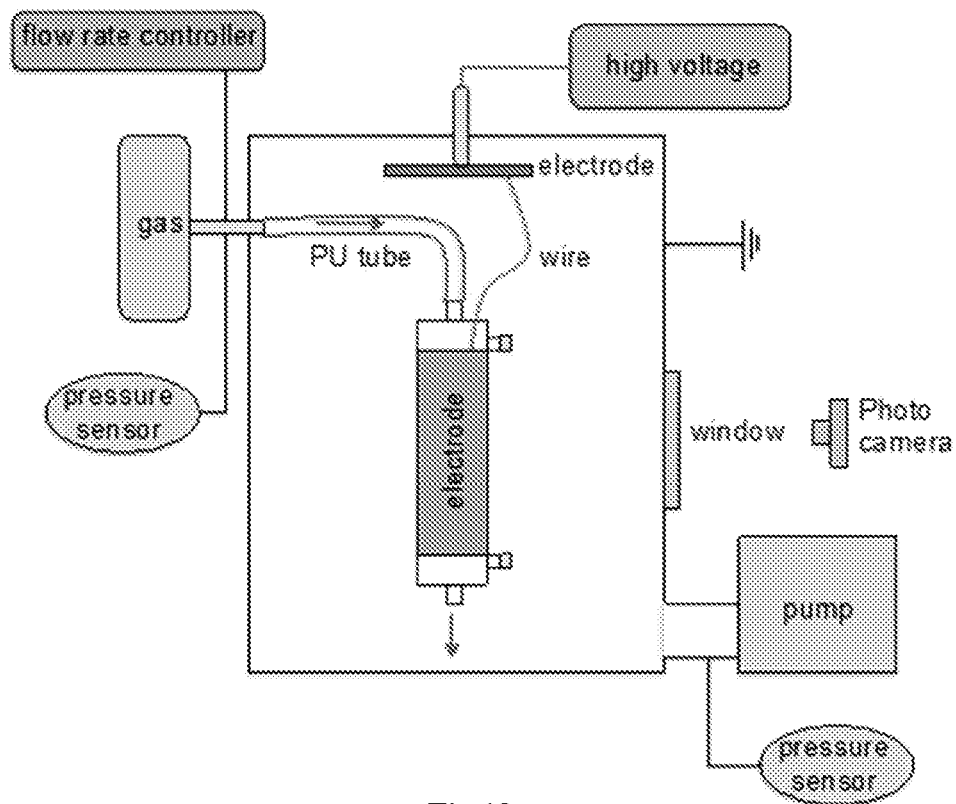
FIG. 13: A schematic diagram of an apparatus for the treatment of a porous object. This apparatus was used to treat an object made up of approximately 10,000 hollow fiber polymer capillaries with 200 micrometer diameter and porous walls with pore size of 10-50 nm assembled in a cassette.

FIG. 13 shows a representation of the apparatus used for treatment. The cassette of hollow fibre polymer capillaries is within a first electrode with two hollow semi-cylindrical electrode components that were placed on the outer surface of the cassette. The cassette with the capillary bundle inside was placed within a vacuum chamber. The cassette inlet was connected to a gas source through a polyurethane (PU) tube. The outlet of the cassette was opened into the vacuum chamber. A pulsed negative bias potential was applied to both components of the first electrode. Earthed second (counter) electrode components were located on the gas feed tube and the vacuum chamber, remote from the cassette. The pressure in the gas inlet and in the vacuum chamber was measured by pressure sensors. A stable pressure of the working gas in the chamber was provided by a gas flow rate controller.

Figure 14:
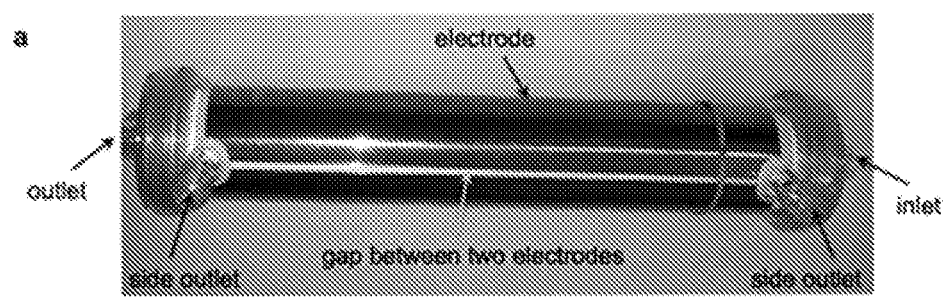
FIG. 14: Photograph of the cassette with two hollow semi-cylindrical electrodes placed on its outer surface, electrically connected together and acting together as the first electrode. When in use plasma can be observed in the capillaries (through the gap between the electrodes) and in the PU tubes connecting the inlet and outlet ports of the cassette to the gas source and the vacuum pump.

Images of plasma brightness distribution, shown in FIG. 14, were taken by a camera through a window in the chamber wall. It will be appreciated that taking images and providing the window and camera may be omitted in other embodiments.

Treatment was performed with pulses of −10 kV and 75 sccm flow rate. The pressure at the gas inlet was 2.3 Torr and 3.0 Torr for the cassettes with open and closed side outlets, respectively. The pressure in the chamber was $10^{-4}$ Torr during plasma treatment, although the pressure inside the capillaries of 200 μm internal diameter was expected to be higher than this, it was not measured directly. Pulse frequencies of 50 Hz, 200 Hz and 400 Hz were used and the treatment time was varied in the range of 1 min-1.5 h. The PU tube had an 8 mm inner diameter and a length of 53.4 cm. Voltage and gas flow rate were varied in the ranges of 0-20 kV and 0-100 sccm, respectively. The pulse duration was 20 μs.

Figure 17:
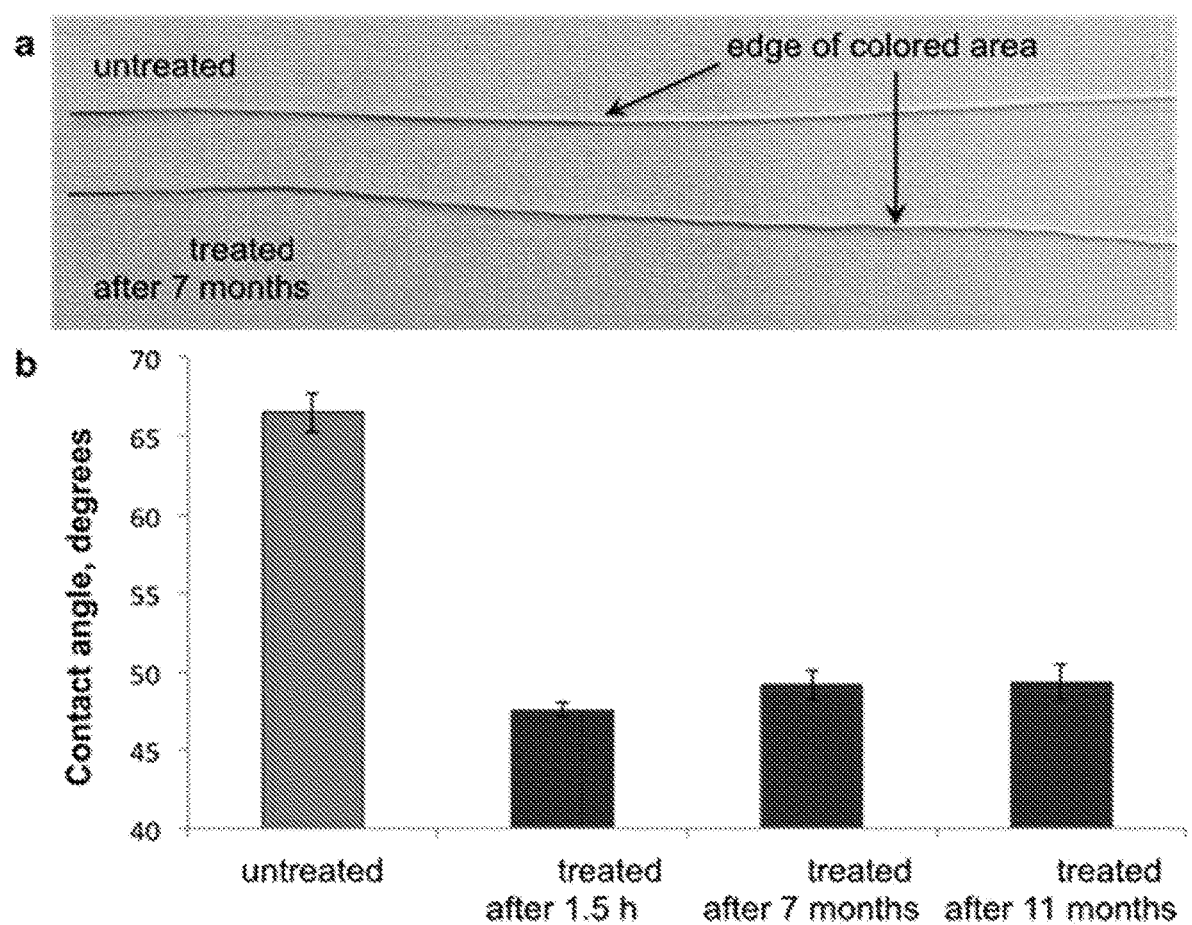
FIG. 17: Shows plots of (a) Capillary rise in untreated and treated capillaries. (b) Contact angles on the inner surface of untreated and treated capillaries measured at various times after the treatment. A very small hydrophobic recovery is observed.

It was found that sealing of the side outlets of the cassette leads to a wider working voltage range and more uniform treatment across and along the cassette compared to the configuration with open side outlets. Both the inner and outer surfaces of capillaries in the bundle were modified by the treatment. The degree of oxidation and carbonisation was higher on the inner surfaces compared to the outer surfaces of the capillaries. The wettability of the treated capillaries was measured and found to be improved by the treatment as shown in FIG. 17.

It was found that the treatment time can be significantly reduced by increasing pulse frequency. For example, the intensity of treatment is about the same after 30 min at 50 Hz and 5 min at 400 Hz.

FTIR-ATR spectra were obtained from the inner and outer surfaces of the untreated and treated PES capillaries using a Hyperion 2000 FTIR microscope (Bruker Optics) in reflection mode with a 20×ATR (attenuated-total-reflection) objective with a hemispherical Germanium crystal.

Figure 15:
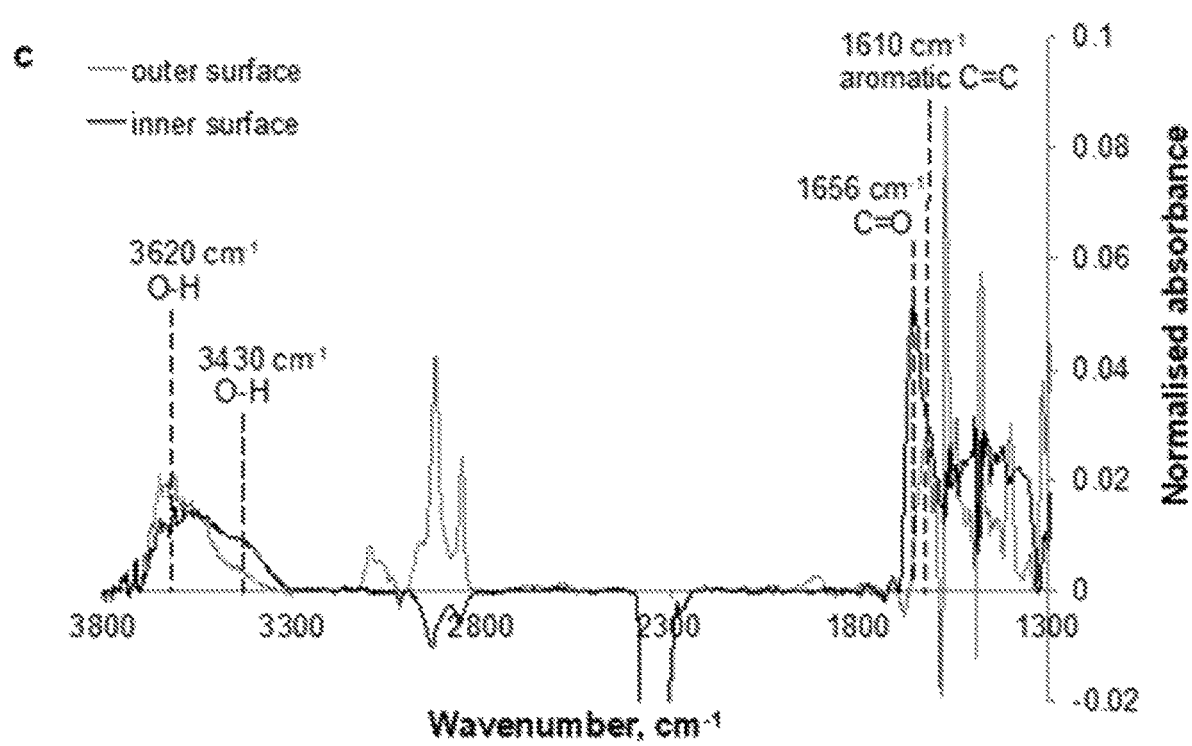
FIG. 15: A plot of a difference between FTIR-ATR spectra of treated and untreated capillaries measured on the inner and the outer surfaces of the capillary. The spectra were normalised on the intensities of the 1578 cm$^{-1}$ vibration line of the corresponding FTIR-ATR spectrum of the treated capillary before subtraction.
Figure 16:
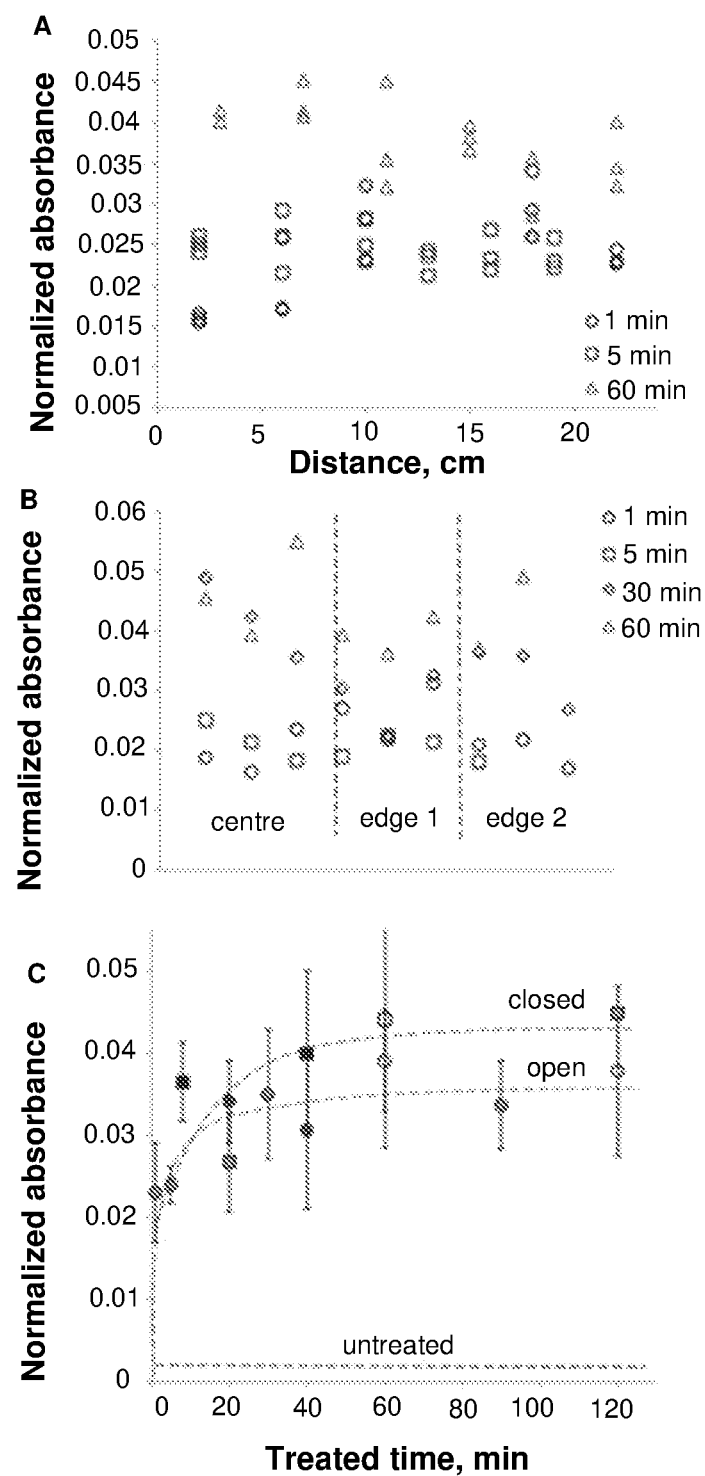
FIG. 16: Shows plots of (a) Intensity of the 1610 cm$^{-1}$ vibration line (aromatic carbon) measured on inner surfaces of untreated and treated capillaries to examine uniformity of treatment along the cassette at various treatment times. The capillaries were chosen from the centre of the cassette and cut open at six different positions along the capillary. Three separate areas were studied in each position. The x-axis indicates the distance from the cassette inlet. (b) Intensity of the 1610 cm$^{-1}$ vibration line measured on the inner surfaces of the capillaries taken from the centre and two opposite edges of the cassette to estimate the uniformity of the plasma treatment across the cassette. The central area of the capillary was investigated. (c) Intensity of the 1610 cm$^{-1}$ vibration line as a function of treatment time for cassettes with open (circles) and closed (squares) side outlets. Open squares and circles correspond to 50 Hz pulse frequency treatment. Light squares and light circles correspond to 200 Hz while dark squares and dark circles represent the capillaries treated with 400 Hz pulse frequency. All FTIR-ATR spectra were normalised on the intensity of the 1578 cm$^{-1}$ vibration line of the corresponding spectrum.

The cassette was cut open and three capillaries were chosen for analysis. One capillary was taken from the centre of the cassette and the two other capillaries were from the opposite edges of the cassette. Six positions along each capillary were chosen (3 cm, 7 cm, 11 cm, 15 cm, 19 cm and 22 cm). In each position, three areas on the inner surface of the capillary were measured. FIG. 15 shows a typical difference in spectra between the treated and untreated capillaries. The spectra were subtracted after normalisation on the intensity of the 1578 $cm^{-1}$ vibration line. The FTIR absorbances showed that the treatment was uniform throughout the cassette and that the treatment intensity increased with increasing treatment time (FIG. 16).

Figure 18:
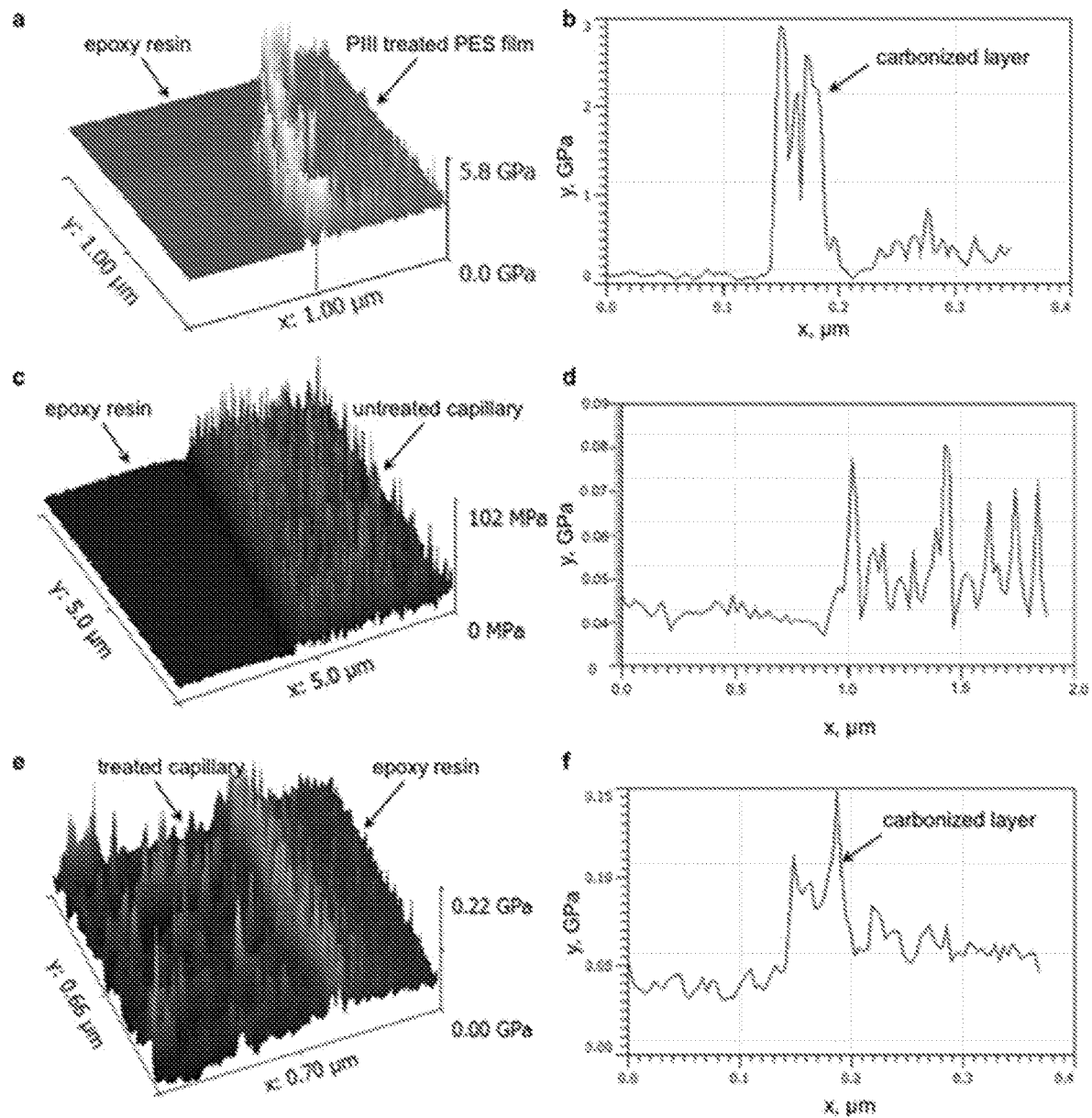
FIG. 18: Shows the results of stiffness measurements using an atomic force microscopy on a cross-section through (a) a PES film treated, at 20 kV for 800 s (c) an untreated capillary and (e) a capillary (inner surface) treated at 10 kV for 30 min, all embedded in epoxy resin. The carbonised layer is observed as an area of increased stiffness on the ion treated samples (a) and (e) whilst no elevation in stiffness at the surface of the untreated sample (c) is observed. Stiffness profiles along a line normal to the surface of (b) the 800 s treated PES film, (d) the untreated capillary and (f) the treated capillary are also shown.
Figure 19:
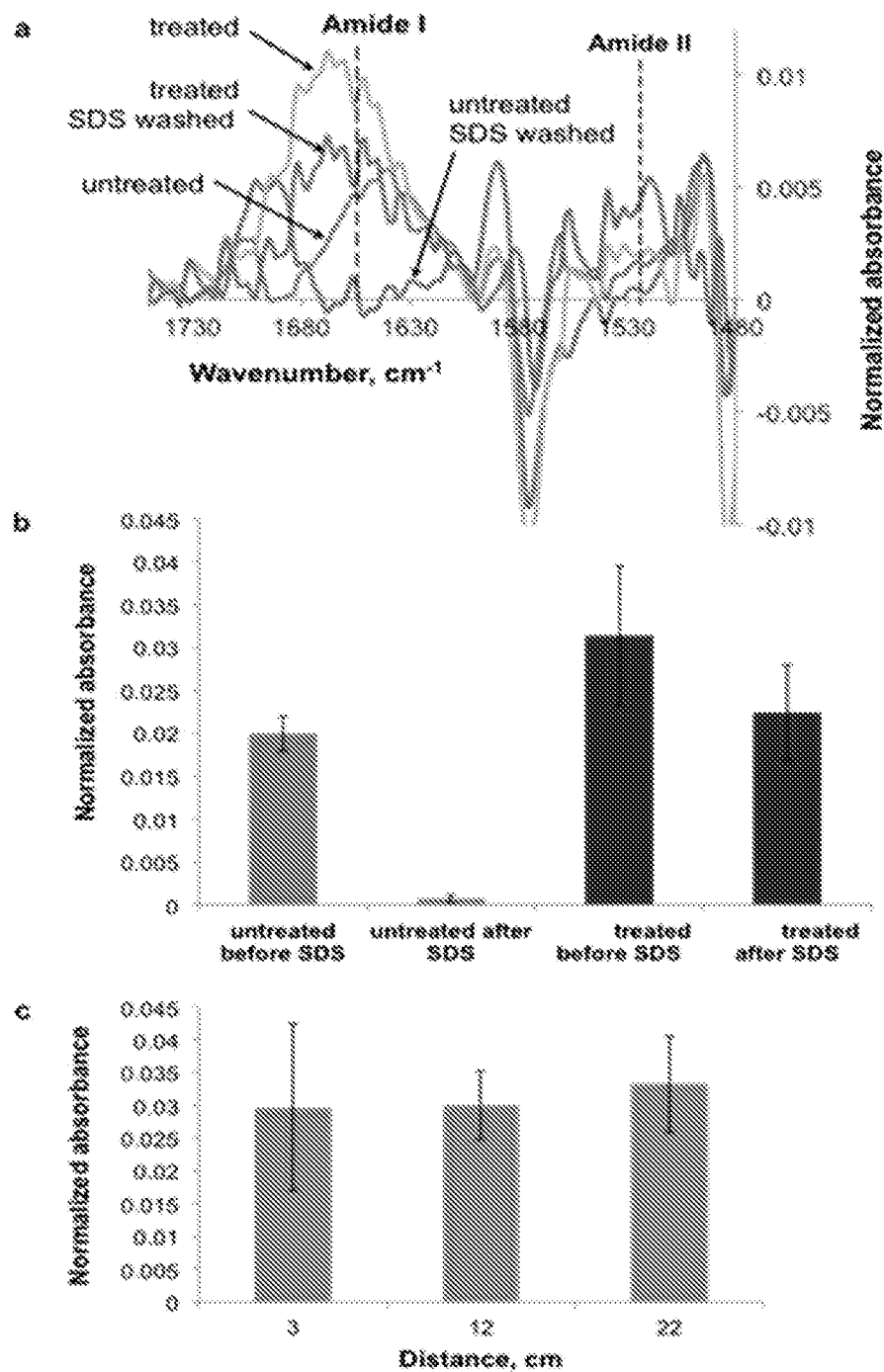
FIG. 19: Shows (a) Difference spectra showing ATR-FTIR signals from protein on the surfaces of untreated and treated capillaries before and after sodium dodecyl sulphate (SDS) washing. Spectra from otherwise identical samples incubated in buffer solution without tropoelastin were subtracted from the spectra of the corresponding samples that were incubated in tropoelastin containing solution. The difference spectra were normalised on the intensity of the 1578 cm$^{-1}$ vibration line from the spectra of the corresponding tropoelastin coated samples. (b) Intensity of Amide I peaks measured on untreated and treated capillaries with tropoelastin coating before and after SDS washing. (c) Intensity of the Amide I peaks as a function of distance along a tropoelastin-coated, treated capillary measured at multiple points at each distance.

Atomic force microscopy measurements of the stiffness as a function of depth below the surface of the fibres obtained from cross-sections of treated capillaries embedded in resin were used as an indicator of the carbonised layer thickness. The measured thickness relates to the energy of bombarding ions. This approach was first verified on a PES film that had been PIII treated for 800 s in nitrogen plasma with 20 kV substrate pulsed bias (20 μs pulse duration and 50 Hz pulse frequency). FIG. 18 shows that the stiffness of the carbonised layer formed on the surface of the PIII treated PES film is significantly higher than the stiffness of the unmodified PES and the embedding epoxy resin. The depth of the carbonised layer was determined as 82.6±9.4 nm (FIG. 18b). The depth of penetration for 20 keV nitrogen ions in PES was calculated to be about 74 nm. The good agreement between the depth determined from the stiffness measurements and the calculation confirmed that stiffness measurements are indicative of the depth of surface modification. A cross-section of an untreated capillary embedded in epoxy resin was used as a negative control. Elevated stiffness was not observed at the interface between the epoxy resin and the untreated capillary (FIGS. 18c and 18d). FIGS. 18e and 18f show the presence of the carbonised layer on the inner surface of the capillary cross-section treated using 10 kV pulsed bias (20 μs pulse duration and 50 Hz pulse frequency) applied for 30 min. The thickness of the carbonised layer formed on the inner surface of the plasma ion treated capillary is 46.4±9.9 nm. According to calculations, the depth of 10 keV nitrogen ions in PES is about 40 nm. This indicates that the energy of the implanting nitrogen ions during the treatment reaches about 10 keV when a negative 10 kV pulsed bias is applied to the conformal first electrodes.

Covalent binding of tropoelastin to the surfaces of capillaries in the treated cassette was verified by its resistance to removal by hot SDS washing. SDS removes physisorbed protein by disrupting all physical interactions, but it cannot break covalent bonds formed between the protein and polymer macromolecules. Treated and untreated capillaries were incubated in tropoelastin solution. Four cassettes (two untreated and two treated) were incubated with tropoelastin (24 μg/ml in PBS, pH 7.4). Tropoelastin solution was pumped through the cassettes for 30 min at 100 ml/min flow rate to insure uniform coverage of the capillaries. Then, the cassettes were stored overnight at room temperature with tropoelastin inside them. On the next day, two cassettes (one untreated and one treated) were washed with 3 L of mQ-water each at water flow rate of 100 ml/min. The last two cassettes were washed for 40 min in 2% SDS at 70° C. and 100 ml/min flow rate and for 500 min at room temperature in mQ-water at the same flow rate as before. All cassettes were dried and cut open. Six different areas along the capillary were chosen for analysis and three FTIR-ATR spectra were measured in each area.

In an example implementation, polyether ether ketone (PEEK) structures were subject to PIII treatment in an apparatus like that described herein with reference to FIG. 11, for affecting host conditions for bone growth and mineralization. The PEEK structures were 3D printed on a 3D printer that operated by filament deposition modelling, with a PEEK filament of 0.2 mm diameter. For cell adhesion assessment, PEEK discs with a diameter of 20 mm and 0.7 mm in thickness were constructed, in two layers consisting of printed bars adjacent to each other. For a proliferation assay, mass gain experiment and scanning electron microscopy (SEM) and energy-dispersive X-ray spectroscopy (EDX) analysis, circular porous PEEK scaffolds with a diameter 20 mm and 0.4 mm thickness with two layers of printed bars of width 0.4 mm separated by a gap of 0.4 mm were constructed.

The PEEK printed structures were treated by immersing in a dielectric barrier discharge in nitrogen gas at 350 mTorr pressure. The discharge was excited by a high voltage electrode consisting of a metal electrode covering the bottom and sides of a conical, borosilicate Erlenmeyer flask (250 ml, neck diameter 25 mm). This structure is analogous to that of FIG. 11, with the Erlenmeyer flask replacing the glass tube of FIG. 11. Negative voltage pulses of 10 kV were applied to the electrode. The pulse frequency was 1500 Hz, the pulse length was 40 µs and the total treatment time was 20 minutes. Following PIII treatment, the PEEK structures were submerged in phosphate buffered saline (PBS) overnight. Then, the scaffolds were washed thrice in excess PBS followed by two washes with excess deionised water and air dried overnight at 4° C. All scaffolds were subjected to an autoclave treatment at 134° C. for 4 min at 30 psi before use.

The wettability of the 3D printed PEEK mesh structures before and after PIII treatment was studied by water contact angle measurement. Ultrapure water (40 µl) was placed onto the UT and PIII treated PEEK discs and mesh. A photographic image was taken, and a tangent was drawn at the line of contact to measure the contact angle.

A Soas-2 osteoblast-like cell line was obtained. The cells were cultured in McCoy's 5A medium supplemented with 15% foetal bovine serum, referred to as culture medium, at 37° C. in a humidified atmosphere with 5% $CO_2$. The cells were passaged regularly to maintain the exponential growth state. To subculture the cells were lifted with 0.25 Trypsin Na-EDTA and reseeded at a lower density.

Adhesion of Saos-2 cells to the untreated (UT) and PIII treated 3D printed PEEK structures was assessed by the AlamarBlue™ (AB) assay. AB is a resazurin-based reagent, which is used to monitor cell viability as a measure of live cell number. Fluorescence intensity was shown to be proportional to the cell number up to 500,000 cells per 700 µl AB solution (data not shown).

The PEEK scaffolds were wetted with 15% FBS in McCoy's 5A medium prior to cell seeding Saos-2 cells were seeded at equal densities of $2\times10^5$ cells/cm$^3$ on top the 3D printed PEEK discs. Cells seeded into tissue culture vessels served as control. The cells were allowed to adhere for two hours before washing twice with culture medium and the cells were then allowed to settle overnight at standard culture conditions. The following day, the discs were moved into new culture vessels and the media was replaced by 10% (v/v) AB containing culture media and incubated for 4 h. After incubation, the fluorescence of the dye was quantified at excitation wavelength of 545-20 nm and emission wavelengths of 600-40 nm. The values for cells in the TC wells were adjusted by a factor of 0.82 to account for the larger surface area of the well compared to the PEEK disc area.

Cell proliferation of Saos-2 cells on the 3D printed PEEK structures was studied by AB assay. The cells were seeded at equal densities of $2.5\times10^5$/cm$^3$ and incubated for 21 days. At day 5, 9, 13, 16 and 20 the media were removed and replaced with 10% AB containing culture media and incubated for 3.5 h. The culture vessel was changed before each measurement to ensure that only the cells on the scaffold were responsible for the reduction of AB. UT and PIII scaffolds incubated in growth media in the absence of Saos-2 cells served as controls. After the incubation with AB solution the scaffolds were washed once with culture media and re-immersed in culture media. After 21 days in culture, the cells were fixed with 70% methanol for 15 mins followed by a 15 min fixation in 100% methanol.

The scaffolds used for the proliferation and mass gain studies were also analysed using SEM and EDX. SEM imaging was performed using a backscattered electron detector to create atomic number contrast images (10 kV-15 kV). EDX spot and area analysis was used to determine which elements were present. Areas (0.4×0.4 mm squares) were analysed on the topmost bar of the scaffolds (both UT and PIII) that had been previously incubated in culture media in the absence of cells or in the presence of cells. Averages of the EDX analyses were taken over the regions for both UT and PIII samples.

As mentioned, the wettability of the 3D printed PEEK discs and porous scaffolds was studied by measuring the water contact angle. Water droplets on the surfaces of the UT discs showed a contact angle of approximately 95 degrees, while on the PIII treated surface the water readily spread across and penetrated minor interstices, so that a sessile droplet did not appear on the surface. The contact angle on the untreated porous mesh structures was 110 degrees, higher than for the disc surface, while for the treated porous mesh the droplet did not appear because the water penetrated the scaffold. SEM analysis of bare UT and PIII treated PEEK structures showed that the surface topology and integrity of the material was not materially compromised by the PIII treatment or autoclaving.

Figure 20:
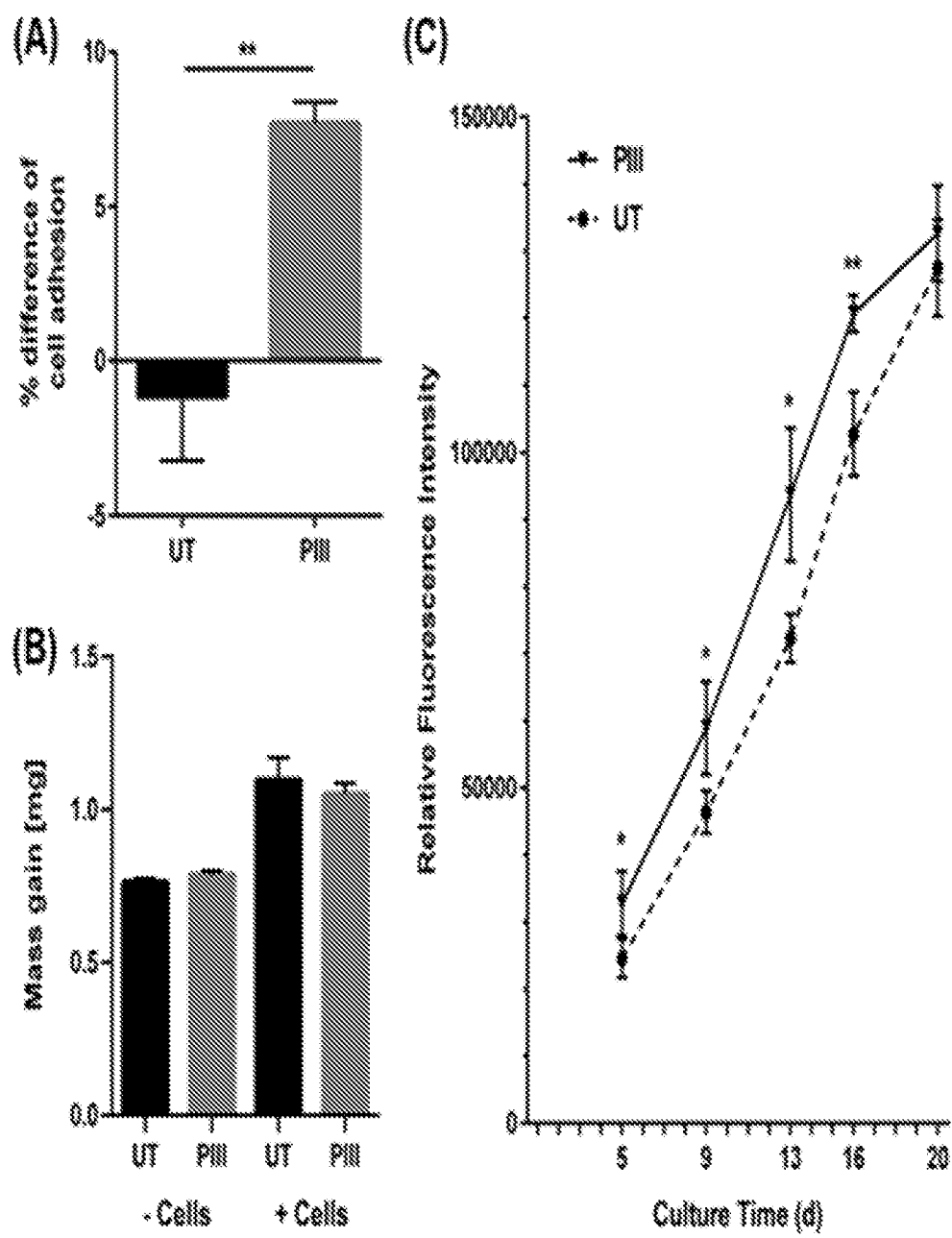
FIG. 20(A) shows a comparison of Soas-2 cell adhesion after 2 h hours of initial incubation to untreated (UT) and PIII treated (PIII) 3D printed PEEK discs. The results are relative to the adhesion to the surface of a tissue culture vessel. Shown is the mean percentage difference and the standard error of the mean of 4 replicates.
FIG. 20(B) shows dry mass gain of 3D printed PEEK mesh scaffolds incubated for 21 days in the absence (−Cells) and presence (+Cells) of Saos-2 cells.
FIG. 20(C) shows the proliferation of Saos-2 cells on 3D printed PEEK mesh as a function of culture time. Shown is the mean value and standard deviation of three replicates. * indicates significance at p<0.05; ** indicate significance at p<0.01.

FIG. 20 shows a comparison of the adhesion of Saos-2 cells to UT and PIII 3D printed discs with the adhesion of cells to standard TC vessels (FIG. 20(A)). Saos-2 cells adhered to untreated 3D printed PEEK less efficiently compared to cells in the tissue culture (TC) vessel. Adhesion was significantly improved by PIII treatment of the PEEK discs compared to cell adhesion to untreated discs and TC vessel.

Untreated and PIII treated PEEK scaffolds that were cultured in culture media in the absence of Saos-2 cells were used as controls and showed no AB reduction change over the course of the experiment. However, untreated and PIII treated scaffolds cultured in media in the absence of cells gained 0.77 mg and 0.79 mg of dry mass, respectively (FIG. 20(B)).

FIG. 20(C) shows that proliferation of cells on PIII treated scaffolds was significantly improved compared to the untreated scaffold after 5 days in culture. The trend continued over the course of the experiment, with significantly better cell growth on the PIII scaffolds except for day 20. After 21 days there was no significant difference.

The UT and PIII mesh scaffolds used for the proliferation experiment as well as the cell free controls were investigated for surface mineralization after 21 days in culture using SEM with EDX analysis.

The SEM analysis, using a backscattered electron detector, showed bright areas and in high magnification amorphous aggregates of relatively high atomic number elements on the surfaces of all scaffolds in various patterns. EDX analysis revealed that the bright areas are rich in calcium, phosphorus and nitrogen. The high atomic number elements Ca and P enabled clear images of mineralized regions to be obtained, which consist of agglomerations of the amorphous aggregates. Nitrogen was not detected in the bare PEEK material after printing. Owing to the lack of crystalline morphology, these nitrogen, calcium phosphate rich aggregates will be termed amorphous calcium phosphate associated protein (ACPAP) aggregates.

Figure 21:
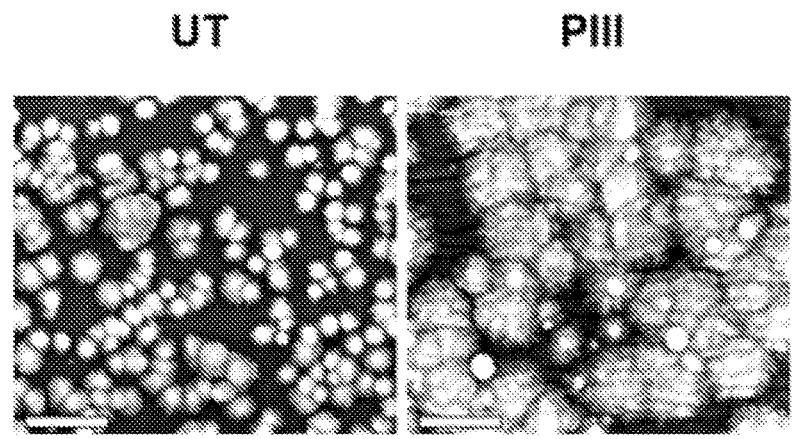
FIG. 21 shows high magnification SEM images of untreated (UT) and PIII treated (PIII) 3D printed PEEK scaffolds incubated in culture medium for 21 days in the absence of cells. Scale bar=5 μm.

ACPAP aggregates were found to be deposited onto all scaffolds in the absence of bone cells. The pattern of deposition in the cell-free environment differed between the two treatment groups. High magnification images of areas with a low density of ACPAP, generally found on the lower bars, revealed that on the UT scaffold the amorphous aggregates appear spherical and elevated from the surface with only a small portion of the aggregates interacting with the surface directly. In contrast, on the PIII scaffold the aggregates appear densely packed and covering a larger fraction of the surface (FIG. 21). The shape of the ACPAP aggregates, which are more spherical as well as elevated from the surface indicates that the UT surface is relatively unfavourable for the deposition ACPAP. PIII treatment appears to make the PEEK surface more attractive for deposition and lateral spreading of ACPAP. In high density areas the ACPAP deposits blend together to form a continuous sheet on top of the surface. Semi quantification of the elements present in deposited material has been carried out via SEM with EDX analysis and shows that there is more calcium, phosphorous and nitrogen on the PIII treated scaffold than on the untreated scaffold (Table 1). Table 1 shows the mean atomic composition in % of EDX area analyses of untreated (UT) and PIII treated scaffolds in the absence and presence of cells.

TABLE 1

Atomic composition of mineralized 3D printed PEEK scaffolds.

| Atomic % | UT No cells | PIII No cells | UT With cells | PIII With cells |
| --- | --- | --- | --- | --- |
| Oxygen | 45.6 ± 4.1 | 51.9 ± 0.7 | 30.0 ± 2.6 | 48.8 ± 1.7 |
| Carbon | 37.8 ± 5.8 | 28.5 ± 1.8 | 49.2 ± 6.4 | 32.2 ± 2.4 |
| Calcium | 4.6 ± 0.6 | 5.8 ± 0.5 | 2.1 ± 0.7 | 4.4 ± 0.4 |
| Nitrogen | 7.4 ± 0.8 | 8.4 ± 0.4 | 16.7 ± 4.7 | 10.6 ± 0.3 |
| Phosphorus | 3.2 ± 0.4 | 3.9 ± 0.3 | 1.5 ± 0.5 | 3.0 ± 0.3 |
| Sodium | 0.9 ± 0.1 | 1.0 ± 0.2 | 0.4 ± 0.1 | 0.7 ± 0.2 |
| Magnesium | 0.4 ± 0.0 | 0.4 ± 0.0 | 0.1 ± 0.1 | 0.3 ± 0.0 |

The fast dehydration during the fixing process led to shrinkage of the deposited mass forming cracks in the ACPAP sheets. The cracks which were wider on the UT scaffold than compared to the more closely spaced and finer cracks on the PIII scaffold.

The presence of cells altered the ACPAP distribution pattern dramatically. The ACPAP deposition on the PIII treated scaffolds almost completely covered the entire cell layer on the upper bars and with few exceptions on the lower bars. On the UT scaffold, ACPAP deposition mainly took place on the upper bars of the scaffold and was sparse with large areas of dark appearing bare cells. The cell layer on the UT surface and its relatively meagre ACPAP covering showed wide cracks similar to those observed on the acellular UT specimen, and sheets of biological material lifting from the surface. In contrast, on the PIII treated scaffold, the cell layer is tightly adhered to the surface and shows only narrow cracks with higher spatial frequency.

Figure 22:
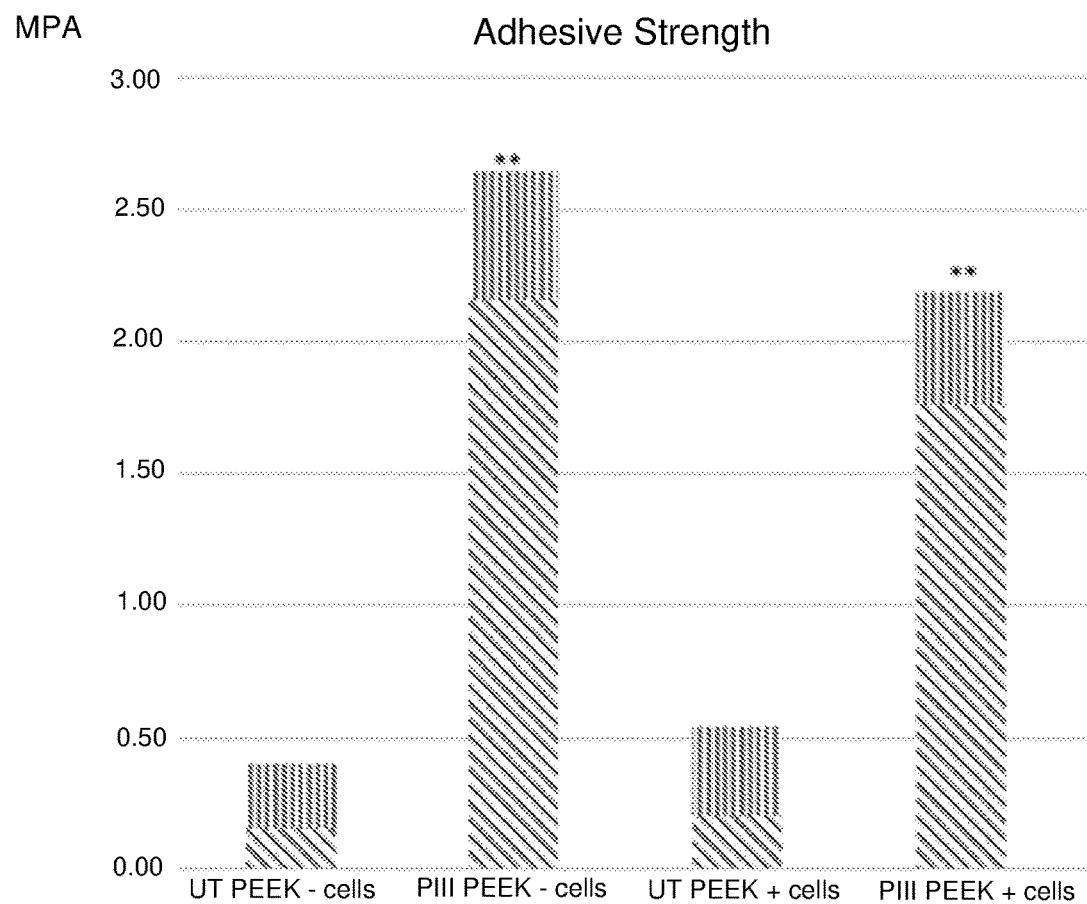
FIG. 22 shows a bar chart of results of a test of adhesive strength of untreated and PIII treated PEEK, in the absence (−Cells) and presence (+Cells) of Saos-2 cells.

FIG. 22 shows results of a test of adhesive strength. The test samples had been incubated in a culture medium with and without Saos-2 cells and then dried out. The mineralised layers with and without cells in both untreated and PIII treated layers were then tested by attaching metal wires of 1.5 mm diameter with ethyl-2 cyanoacrylate adhesive and finding the stress in the wire that caused the wire to be pulled off. In each case failure in the untreated samples was between the PEEK and the mineralised layer. Failure in the PIII samples was mostly within the cell layer where cells were present, and where they were not present, failure was sometimes at the PEEK interface and sometimes at the interface with the wire. The lower bar of the columns (diagonal patterned part) represents the pull off strength for the adhered wire. The top bar of the columns (horizontal patterned part) represents an error bar (the error extends an equal distance below the top of the lower bar). The ** refers to statistical significance at the level of 0.01 (99 percent certainty). As before, the PIII refers to plasma immersion ion implantation treated and UT refers to untreated, that is, as received PEEK.

As described above, using PIII treatment, improved bioactivity of 3D printed PEEK scaffolds, by successfully rendering the scaffold surface from hydrophobic to hydrophilic. PIII treatment of PEEK also increased the deposition of amorphous calcium phosphate associated protein (ACPAP) onto the surface from the culture medium in the absence of cells. PIII facilitated covalent binding through the introduction of persistent radicals in the surface, enabling strong attachment of mineralized layers by binding the protein content of the ACPAP. PIII treatment also increased the adhesion and proliferation of osteoblast-like Saos-2 cells. The cells show earlier and more extensive mineralization than on the untreated surface. The cell layer with its associated mineralization is also more strongly bound to the surface, potentially leading to an implant better able to withstand the stresses encountered when implanted in the body.

Figure 23:
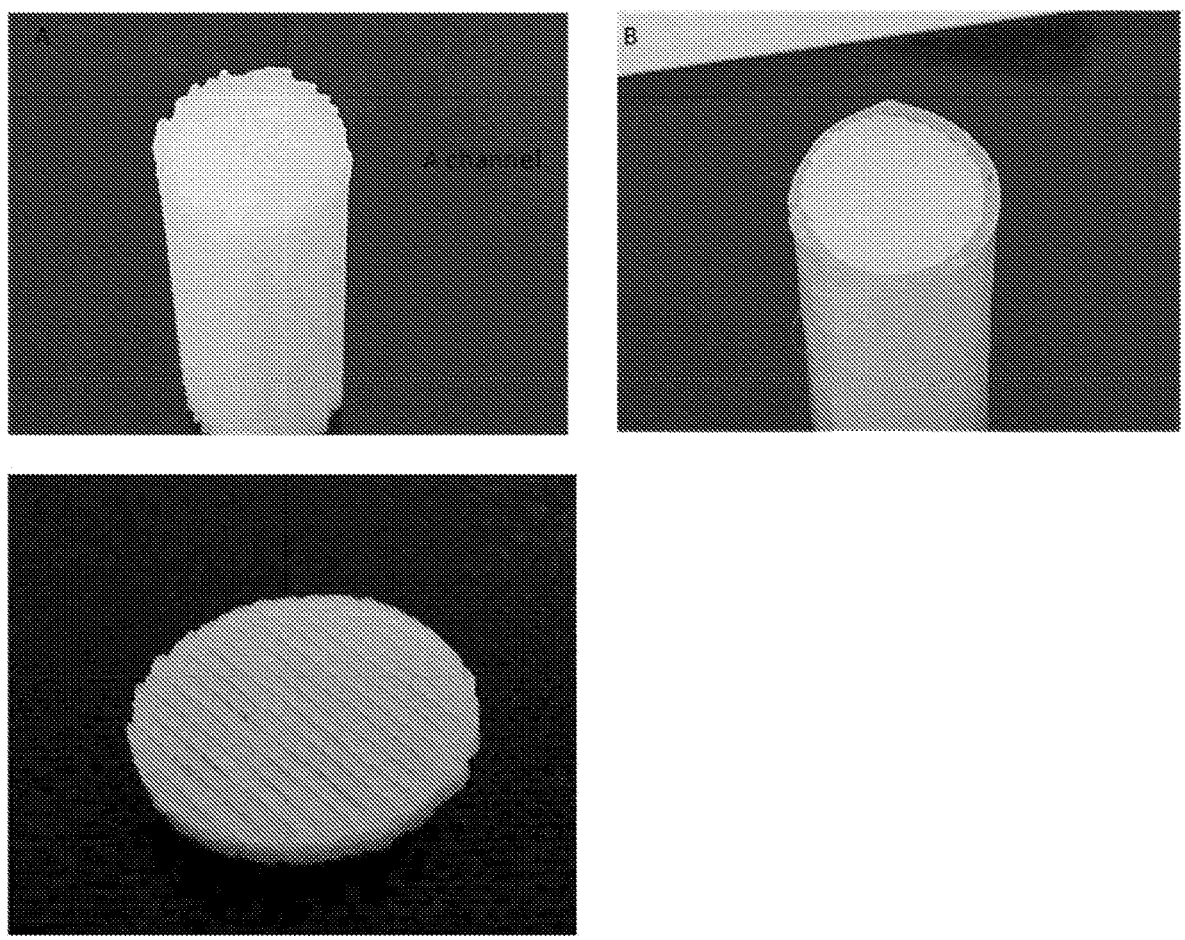

In an example implementation, polystyrene scaffolds were subject to PIII in an apparatus like that described herein with reference to FIGS. 13 and 14, for affecting the expansion of human mesenchymal stem cells (hMSCs). The scaffolds with a pore size of 239.8-263.9 µm and filament size of 348.2-352.1 µm were 3D printed using high impact polystyrene (HiPS) filaments via an extrusion 3D printer. The optimized extruder temperature was 245° C. and the bed temperature was 110° C. The scaffolds were printed in both column (30 mm length, 10 mm diameter) and mesh (1 mm thickness, 10 mm diameter) forms as shown in FIG. 23.

Figure 24:
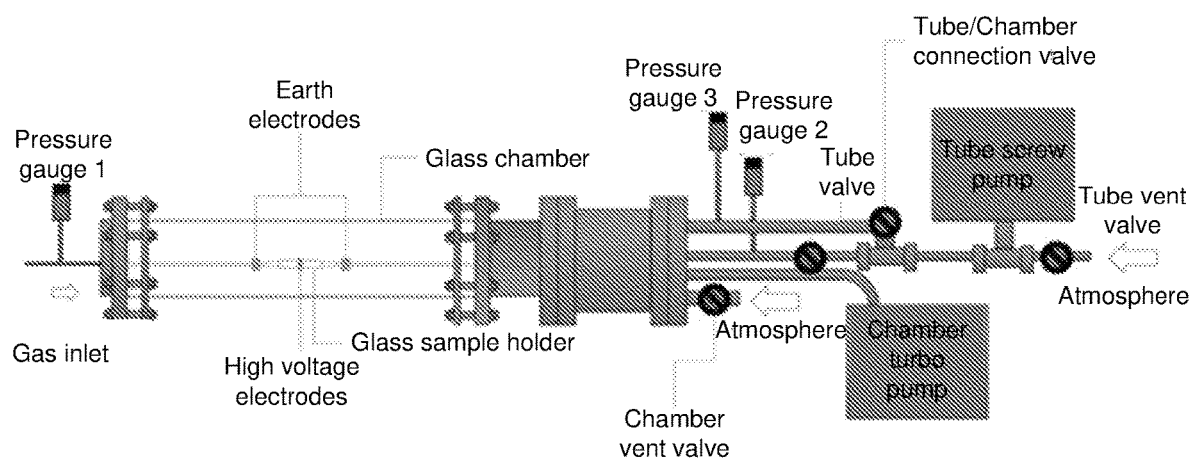
FIG. 24 shows a schematic illustration of a customized PIII system used for the activation of 3D printed scaffolds.

Plasma immersion ion implantation (PIII) treatment of the additively manufactured porous scaffolds was performed using a custom-made, tubular PIII system composed of two separate vacuum lines connected to inner (sample holder) and outer glass chamber. The design of this system is schematically shown in FIG. 24. The outer glass chamber and the glass sample holder were pumped down using a turbo molecular pump and a screw pump, respectively. The pressure at both ends of the glass sample holder was measured using pressure gauges as indicated in FIG. 24. The pressure at both ends of the glass sample holder was controlled through increasing the mass flow rate of the gas used and building up pressure resistance by closing the tube valve. The system consisted of a negative high voltage electrode and two earth electrodes. Both earth electrodes were placed 20 cm away from the centre of the negative high voltage electrode. The plasma was discharged between the high voltage electrode and the two earth electrodes. The negative high voltage electrode was connected to a pulsed power supply.

Figure 25:
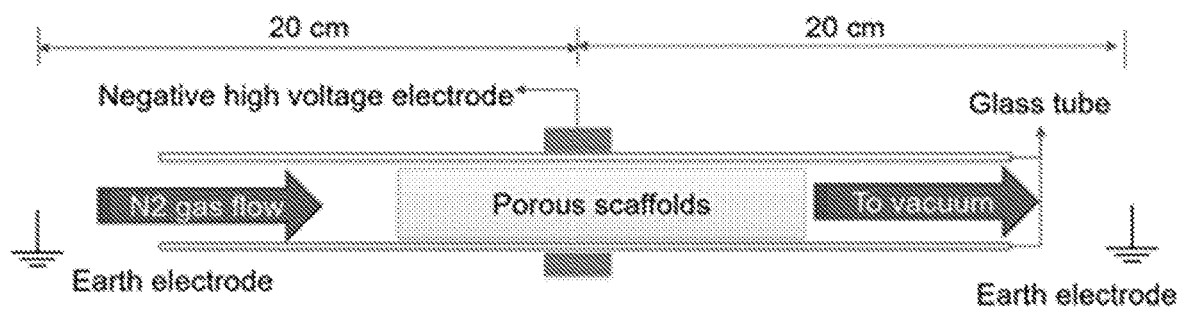
FIG. 25 shows a schematic illustration of the scaffold and electrode positions in the custom-made PIII system.
Figure 26:
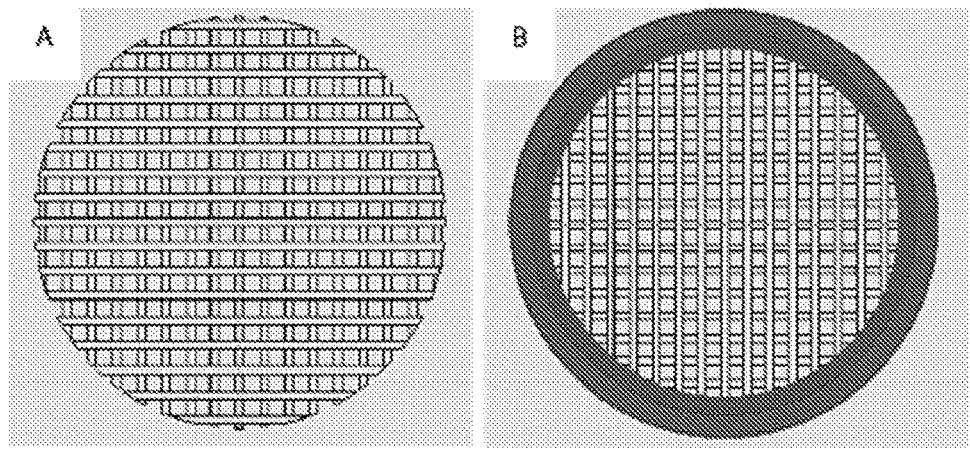
FIG. 26 shows assembly designs for plasma immersion ion implantation of porous 3D printed scaffolds. A: without a shell and silicone sealing; B: with a shell and silicone sealing.

The 3D printed scaffolds were loaded into the middle of the glass sample holder as shown in FIG. 25. Nitrogen gas with a flow of 0.5 standard cubic centimeters per minute (sccm) was injected through a mass flow controller into the tubular sample holder after a base pressure of at least $1.2\times10^{-1}$ Torr was achieved. The pressure in the outer glass chamber was maintained below $5\times10^{-3}$ Torr to prevent arcing at the high voltage electrode. The inlet and outlet pressures were then adjusted by closing the tube valve until they reached the desired stable pressure. PIII was achieved by optimizing the scaffold assembly, high voltage pulses, and pressure. Two different designs for assembling of scaffolds in the sample holder were evaluated and optimized first to achieve plasma activation inside their porous structure. The designs are shown in FIG. 26.

The sample assembly configuration was optimized to achieve nitrogen plasma discharge directly inside the porous scaffolds for PIII treatment. The plasma generation was first examined visually using an optical camera monitoring the PIII discharge. Plasma intensity indicated the degree of collisions by the emission of the light. For this initial step, the light intensity difference was sufficient to visually examine the uniformity of the discharge. The scaffold as per FIG. 26A without an inbuilt shell and silicone sealing resulted in a relatively weak plasma discharge inside the scaffold (in comparison to the scaffold as per FIG. 26B) with localized intense discharges along the outer regions of the scaffold, where a gap between the scaffolds and the glass sample holder was present. In this case, nitrogen gas preferred to flow around the scaffolds rather than flowing inside the pore network structure because the pressure resistance of porous material was higher than that of its external environment. In this case, the plasma was neither easily discharged nor stable once it was generated. A HiPS inbuilt tubular shell was designed to fill the channels on the outer wall of the scaffold. The gap between the scaffolds and the glass tube holder was also minimized using a silicon tube sealing. This approach substantially eliminated the issue of inhomogenous plasma discharge.

Optimization of high voltage for PIII treatment of the column scaffolds was carried out by the application of HV pulses in a range of 4 kV to 8 kV, while the frequency and pulse width were kept unchanged at 3 kHz and 20 μs respectively. The flow rate was kept at 0.5 sccm and the pressure at inlet and outlet was kept around 1.0 Torr. During PIII treatment, C—C bond in polymeric materials is broken due to the bombardment of positive ions accelerated by the electric field. Radicals are formed within the polymeric structure as a consequence. The highly reactive radicals migrating to the surface can react with atmospheric oxygen and form R—OH groups once the PIII-treated samples are exposed to air. R—OH is a key signature of the PIII treatment, which has a FTIR broad absorbance peak between 3300-3500 $cm^{-1}$. This peak was used to evaluate the success of the PIII treatment and determine whether the treatment was homogeneous along the length of the scaffolds.

Figure 27:
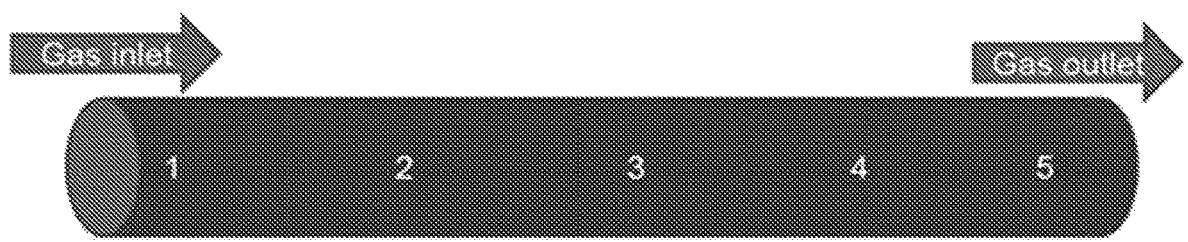
FIG. 27 shows the positions for Micro ATR FTIR measurements carried out on opened scaffolds after PIII treatment.

A micro attenuated total internal reflection Fourier transform infrared spectrometer was used for spatial-resolved analysis of the surface chemistry of untreated and PIII-treated scaffolds. All FTIR measurements were carried out using samples aged for 1 week after PIII treatment. The instrument was equipped with an optical microscope and an ATR crystal covering an area with a diameter of 100 μm, which is smaller than the filament size of scaffolds (348.2-352.1 μm). The scaffold samples were opened along their long axis providing easy access for analysis of the internal networks of the scaffolds. The top layer of the cross section was removed by surgical blades without damaging the second top layer. Therefore, the ATR crystal was able to access the PIII-treated surface of the filament rather than the cross-section of the filament, which was untreated. Five positions were measured for uniformity evaluation as shown in FIG. 27. At each position, the ATR crystal was placed on the filament, and 30 scans were taken at a resolution of 4 $cm^{-1}$. Nine separate areas were studied in each position. The spectra were normalized on the C—H bond at 1493 $cm^{-1}$, and the height of R—OH peaks, a broad absorbance peak between 3300-3500 $cm^{-1}$, for untreated and PIII treated samples were the subject of statistical analysis.

Figure 28:
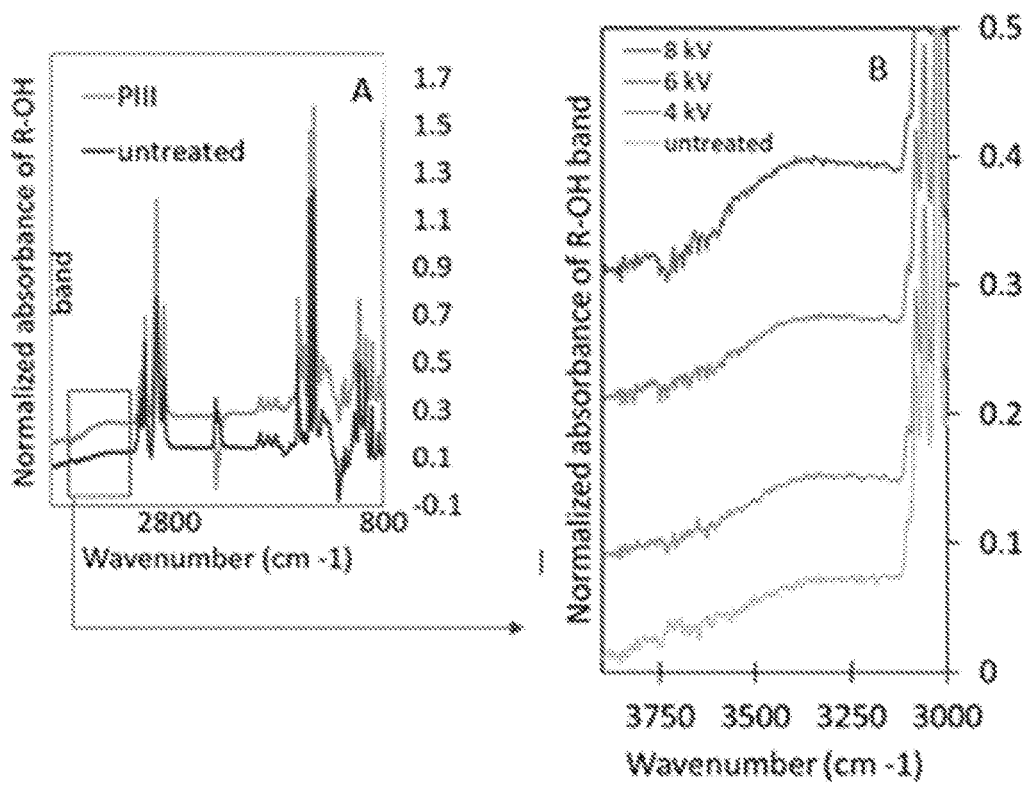
FIG. 28 shows A) Representative FTIR spectra for untreated and PIII-treated samples obtained in the full wavelength range; B) Representative FTIR spectra in the region of the R—OH bond vibrations for untreated and PIII-treated samples prepared at different voltages.
Figure 29:
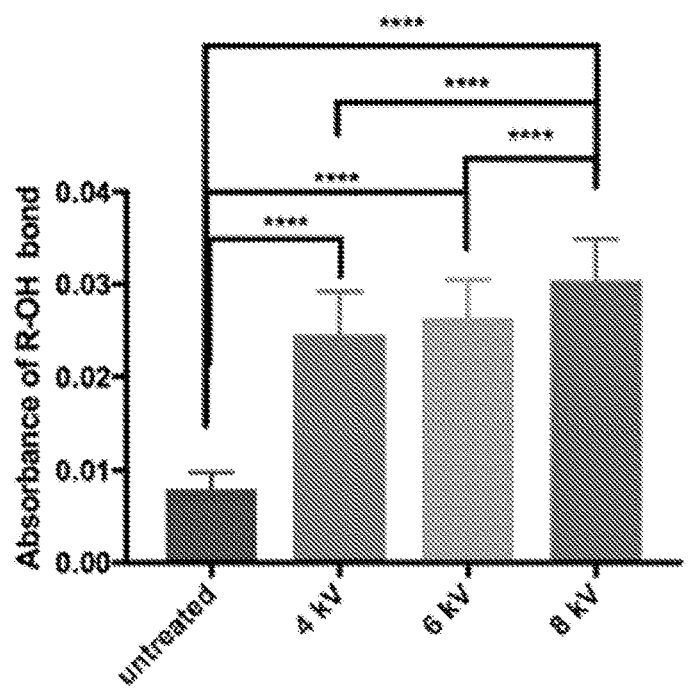
FIG. 29 shows the absorbance of R—OH in the untreated scaffolds (n=15) and the PIII-treated scaffolds at 4, 6, and 8 kV (n=45).

In FIG. 28, normalized absorbance values from the measurement made at different positions were pooled together to evaluate the extent of PIII treatment as a function of applied high voltage. For all the high voltage values, the normalized absorbance values of R—OH were significantly higher than that of the untreated HiPS scaffolds. For example, the absorbance of R—OH peak at 8 kV was 3.8 times greater than that of the untreated control as shown in FIG. 29.

Figure 30:
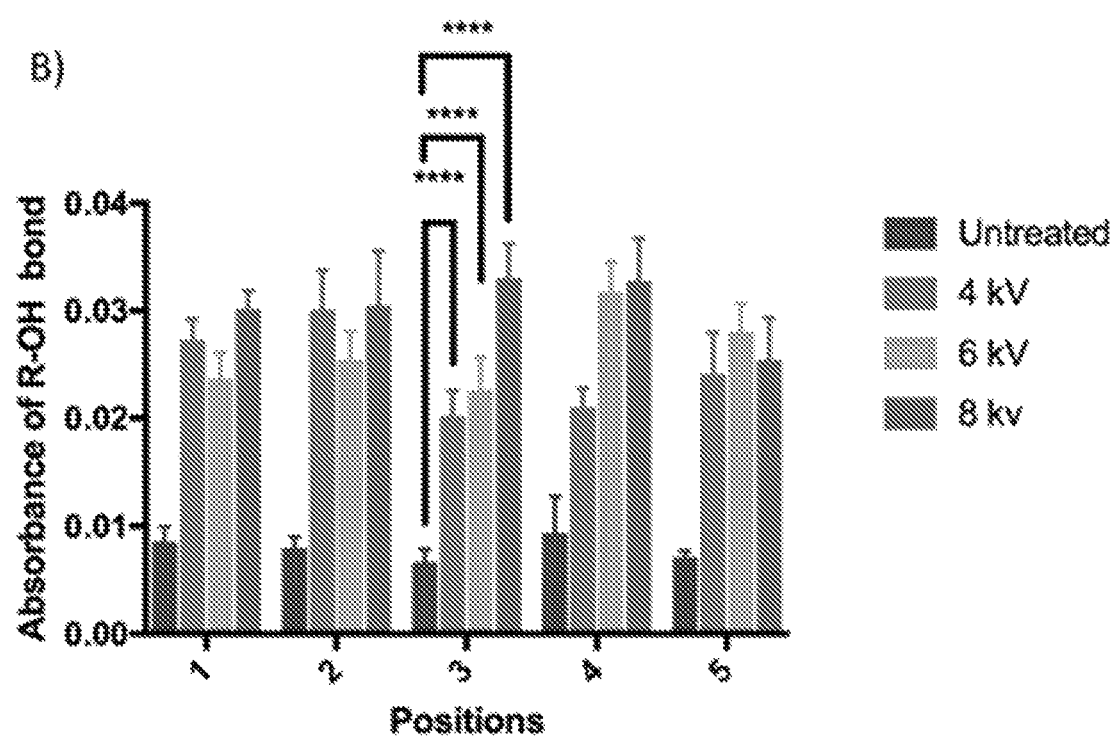
FIG. 30 shows the absorbance of R—OH at different positions of the untreated scaffolds and the PIII treated scaffolds at 4, 6, 8 kV (n=9 for PIII-treated samples, n=3 for untreated samples).

To evaluate the homogeneity of the PIII treatment, FTIR measurements were carried out at various locations along the length of the scaffold. The absorbance values of R—OH peaks for PIII-treated scaffolds were significantly higher than that of the untreated sample for all the locations regardless the voltage applied (FIG. 30). It can therefore be concluded that substantially the entire structure of the scaffolds was successfully PIII-treated using the custom-made PIII system, enabling a plasma discharge to form in the internal porosity of the scaffolds. Of particular importance is position 3 situated in the middle of the scaffolds. The significantly higher R—OH absorbance values for this position provide evidence that even the centre of the scaffold is PIII treated successfully. The uniformity of PIII treatment in the scaffolds can be evaluated by comparing the absorbance of R—OH measured at different positions of untreated scaffolds and the PIII treated scaffolds at 4, 6, 8 kV (FIG. 30). The uniformity was not observed for scaffolds PIII-treated at 4 and 6 kV. The absorbances of R—OH peaks measured at position 3 for scaffolds PIII-treated at 4 kV were significantly lower than that at position 1 and 2. For scaffolds PIII-treated at 6 kV, a significant decrease was observed on the absorbance of R—OH peaks at position 3 compared to that of position 4 and 5. The scaffolds were not homogeneously PIII treated at 4, 6 kV. In contrast, no significant difference in the absorbance of the R—OH peaks for the scaffold PIII-treated at 8 kV was observed between positions 1-4. Moreover, the peaks of R—OH in the scaffold PIII-treated at 8 kV were significantly higher than for those treated at 4, 6 kV. The treatment at 8 kV, was, therefore, the most intense (FIG. 30). As position 1 and 5 were near the ends of the scaffolds, the less treated part could be easily removed in practical applications to keep the uniformly treated part. Therefore, the entire pore network of a 3D printed porous scaffold can be uniformly PIII-treated using the presented strategy.

Figure 31:
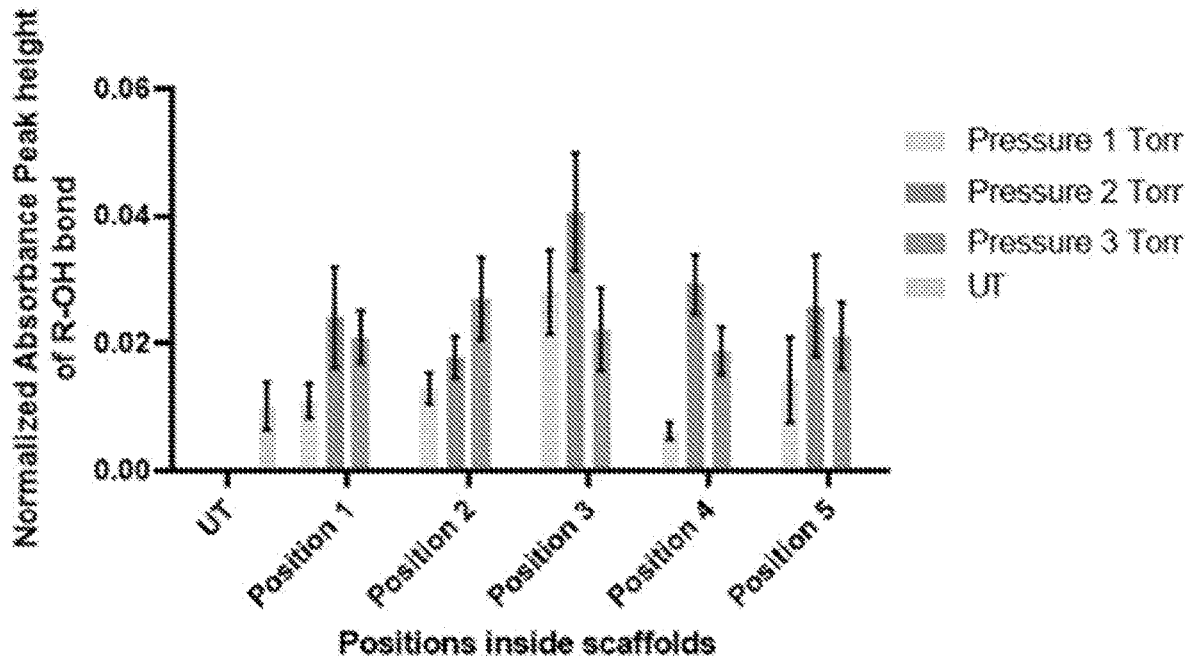
FIG. 31 shows normalized absorbance values for R—OH (3300-3500 cm$^{-1}$) measured on the surfaces of untreated and PIII-treated scaffolds at various PIII treatment pressures (HV=8 kV, n>=5, pressure from 1 to 3 Torr). All FTIR-ATR spectra were normalized to the absorbance of C—H bond at 1493 cm$^{-1}$.

The column scaffolds were replaced by 30 scaffold disks stacked together in the glass tube sample holder without changing the assembly design. PIII treatment in the scaffold disks was achieved by varying the working pressure, measured at the outlet of the glass sample holder, from 1.0 to 3.0 Torr while other previous optimized parameters were kept unchanged (high voltage: 8 kV; flow rate: 0.5 sccm; frequency: 3 kHz; and pulse width: 20 µs). To examine the uniformity of PIII treatment along the scaffold's assembly at various PIII treatment pressures, the surface chemistry of the samples along the length of the assembly was analysed using FTIR. The measurements were taken at different positions inside the scaffolds assembly from inlet to outlet at 5 different positions and the results are shown in FIG. 31. The normalized absorbance of R—OH bond increases upon PIII treatment at working pressures of 2 and 3 Torr for all the positions. The FTIR data also show that PIII treatment at a working pressure of 3 Torr results in the most homogenous modification throughout the scaffolds from inlet to outlet.

The surface wettability of untreated and PIII-treated scaffolds was qualitatively interpreted via a penetration test of a water droplet as well as the immersion of scaffold samples in MilliQ water. Wettability evaluation of untreated and PIII-treated scaffold disks was carried out by placing the samples into MilliQ water. The wettability of samples was also assessed via evaluating the penetration of water droplets (1 µL) placed on the surfaces of scaffold disks within 1 hour after PIII treatment. These tests were carried out using an optical goniometer. To evaluate the changes of wettability over time, samples were tested at 1 hour, referred to as fresh, and 1 week time points from the PIII treatment. As observed, after PIII treatment, the scaffolds become hydrophilic and they sank into the water in contrast to the untreated scaffold that is hydrophobic and floats on the water. These results are also in agreement with optical images of water droplets placed on untreated and PIII treated scaffolds and imaged after 3.5 seconds. The water droplet placed on the untreated scaffolds remained on the surfaces, whereas those placed on PIII-treated scaffold disks rapidly penetrated the scaffold structure. The results indicated that the PIII treatment successfully tuned the wettability of internal surfaces though out the scaffolds assembly, and scaffolds remained hydrophilic after one week.

Scanning electron microscope images of untreated and PIII-treated scaffold disks. Images were obtained at a voltage of 10 kV. The working distance was 5 mm. The images indicated that PIII treatment of scaffolds did not result in substantial deformation, melting or noticeable changes in their microstructures and surface topography.

Figure 32:
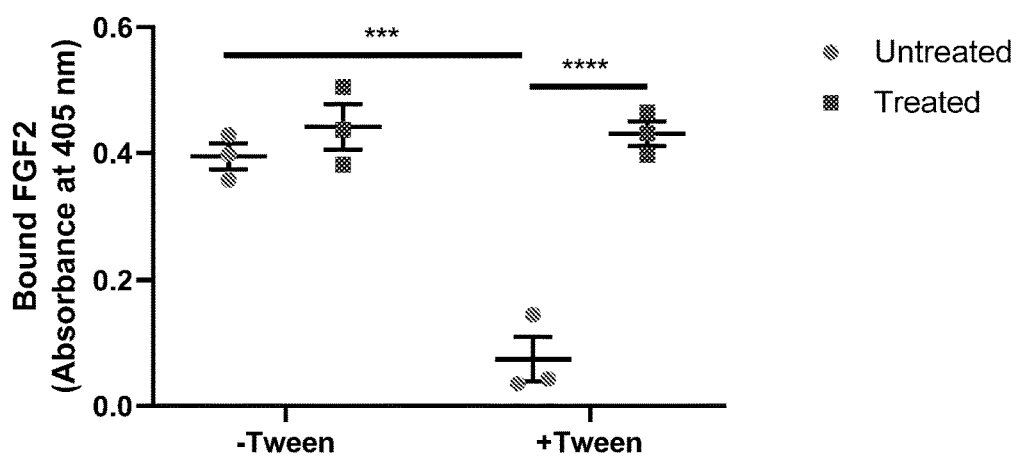
FIG. 32 shows ELISA detection of surface-bound FGF2 on untreated and PIII-treated scaffolds before and after detergent washing.

3D untreated and PIII-treated HiPS scaffolds placed in 48-well plates were coated with 2 µg/mL fibroblast growth factor 2 (FGF2) in phosphate buffered saline (PBS; 10 mM phosphate, 150 mM NaCl) for 3 hrs at room temperature (RT). Samples were then washed with PBS twice to remove unbound protein. Half of the protein-coated samples were immersed in 2% (v/v) Tween-20 and heated to 60° C. for 20 min, then washed with PBS three times. All samples were blocked with 3% (w/v) bovine serum albumin (BSA) for 1 hr at RT, then rinsed once with PBS. A mouse monoclonal anti-FGF2 antibody (1 µg/mL) was added to samples for 1 hr at RT, and washed off three times with PBS. A 1:5000 dilution of anti-mouse HRP-conjugated secondary antibody was added to samples and incubated at 4° C. overnight. Samples were washed three times with PBS, further rinsed in a large volume (50 mL) of PBS, and transferred to a fresh 48-well plate. ABTS substrate (300 µL) was added to each sample for 20 min at RT, with 100 uL aliquoted for absorbance reading at 405 nm. Surface-bound FGF2 protein can be detected using a specific anti-FGF2 antibody following a standard ELISA protocol. To determine the extent of covalent protein binding on the 3D scaffolds, protein-coated untreated and PIII-treated scaffolds were subjected to stringent wash conditions with Tween-20 detergent at a high temperature (60° C.). This washing step is known to remove physiosorbed biomolecules, while retaining those that are covalently-linked to the surface. Before Tween washing, comparable levels of FGF2 were detected on the protein-coated untreated and PIII-treated scaffolds (FIG. 32). However, after Tween washing, majority of the FGF2 on untreated scaffolds were removed. In contrast, the FGF2 on PIII-treated scaffolds were fully retained. This result provides evidence that PIII treatment of the 3D scaffolds enables covalent immobilisation of adhered biomolecules such as FGF2.

Fluorescently labelled IgG were used as a model molecule to assess the covalent attachment and to visualize the homogeneity of PIII treatment on HiPS scaffolds. Detergents Tween 20 remove proteins physiosorbed on HiPS scaffolds but are not able to detach covalently bound proteins. To further confirm the covalent attachment and to demonstrate the homogenous distribution of covalently attached biomolecules onto PIII-treated scaffolds, Cyanine5 conjugated goat anti-rabbit IgG protein (4 µg/ml) was used as a model molecule. The untreated and PIII-treated scaffolds were incubated in IgG/PBS solution for 2 h at room temperature. Protein-coated samples were immersed in 2% (v/v) Tween-20 and heated to 60° C. for 60 min to remove physiosorbed IgG molecules. The samples were then washed with PBS three times. Fluorescence profile of the scaffolds were obtained using a confocal microscope for visualisation of the protein attachment. The laser was set at wavelength of 640 nm and laser power of 2.0. Homogenous presence of fluorescently-labelled IgG covalently attached to the PIII-treated scaffolds was confirmed by showing its resistance to Tween 20 washing in the PIII-treated scaffolds group, whereas removal of most physically adsorbed IgG from untreated HiPS scaffold surfaces was evident.

Cell proliferation was assessed on the 3D HiPS scaffolds. Human mesenchymal stem cells (hMSCs) derived from bone marrow (Donor: female, age 35) were cultured in Alpha Minimum Essential Medium (αMEM) supplemented with 10% FBS (v/v), 1% (v/v) L-glutamine, 50 U/mL penicillin/streptomycin at 37° C. in 5% $CO_2$. Untreated and PIII-treated 3D scaffolds were disinfected under UV light in a Biosafety Cabinet II (BSCII) for 30 minutes each side and washed 3 times with PBS. Scaffolds were pre-wetted by overnight incubation in PBS. Before cell seeding, scaffolds were dried using sterile kimwipes and placed in a non-tissue culture treated 48-well plate. Glass holders were disinfected in 80% (v/v) ethanol overnight, washed 3 times with PBS and soaked in PBS overnight. Glass holders were dried with sterile kimwipes and used to hold scaffolds down in wells. Trysinised passage 6 hMSCs were centrifuged for 5 min at 270 g and resuspended in culture media at a density of 5,000 cells per 100 µl. A 100 µl droplet of cell suspension was pipetted on top of the 3D scaffold and allowed to be drawn into the scaffold by capillary action. Seeded scaffolds were incubated for 2 h at 37° C. in a 5% $CO_2$ incubator to allow cell attachment. After this time, an additional 400 µl CM was pipetted into the wells. Media was changed every other day. Cell numbers on scaffolds were quantified at days 1, 4, 10 and 14 post-seeding. At each timepoint, media was removed from the wells with scaffolds. Scaffolds were rinsed once with PBS, then moved to a new 48-well plate and frozen at −80° C. Once all timepoints had been collected, scaffolds were thawed and 250 µL of CyQUANT™ working reagent was vigorously pipetted into each scaffold and allowed to incubate at RT for 15 min in the dark. After incubation, 200 µL was transferred to a 96-well plate for fluorescence measurement (emission/excitation: 520/480) using a plate reader. Cell numbers were calculated using a standard curve.

Cell imaging was used to determine uniformity of cell proliferation throughout the scaffolds. Untreated and PIII-treated scaffolds were imaged at days 1, 4, 7, 10 and 14 post-seeding. Scaffolds were washed with PBS and fixed with 10% (v/v) formalin for 20 min at RT, followed by three PBS washes. Quenching was carried out with 0.2 M glycine for 20 min at RT, followed by 3 PBS washes. Cells were permeabilised using 0.1% (v/v) Triton X-100 for 5 min at RT, washed thrice with PBS and incubated with NucBlue™ Live ReadyProbe™ and ActinRed™ 555 ReadyProbe™ (Thermo Fisher Scientific) for 15 min at RT. Finally, the scaffolds were washed 3 times with PBS. The scaffolds were imaged using an upright widefield fluorescence microscope with stitching function. Images were processed and a two-way ANOVA was performed with Tukey's multiple comparison test to evaluate statistical significance. Statistical significance was set at $p<0.05$. Data are shown as average of minimum 3 independent replicates with error bars indicating standard deviation.

Figure 33:
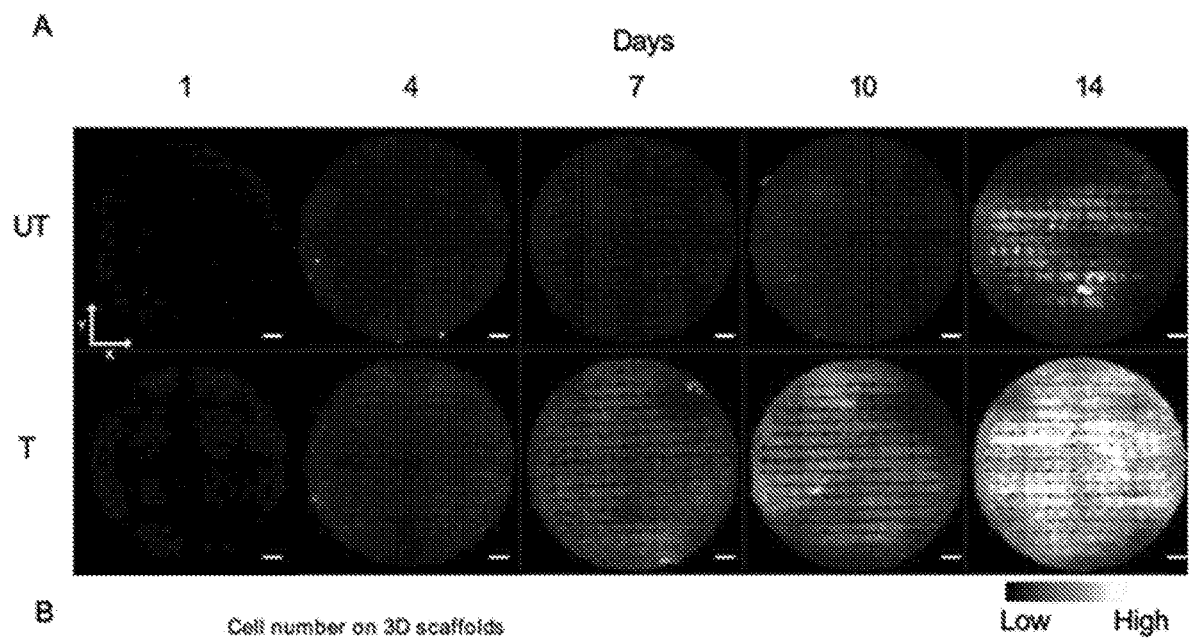
FIG. 33 shows human MSC proliferation on untreated and PIII-treated scaffolds. (A) Confocal images of hMSCs on the top side of untreated (UT, top) and treated (T, bottom) scaffolds over 1, 4, 7, 10 and 14 days post-seeding. Cells were stained for F-actin, with low levels of staining appearing black and high levels of staining appearing yellow. Scale bar: 1 mm. (B) Cell numbers on untreated and treated scaffolds over 14 days. ( p<0.01; ** p<0.0001).
Figure 33:
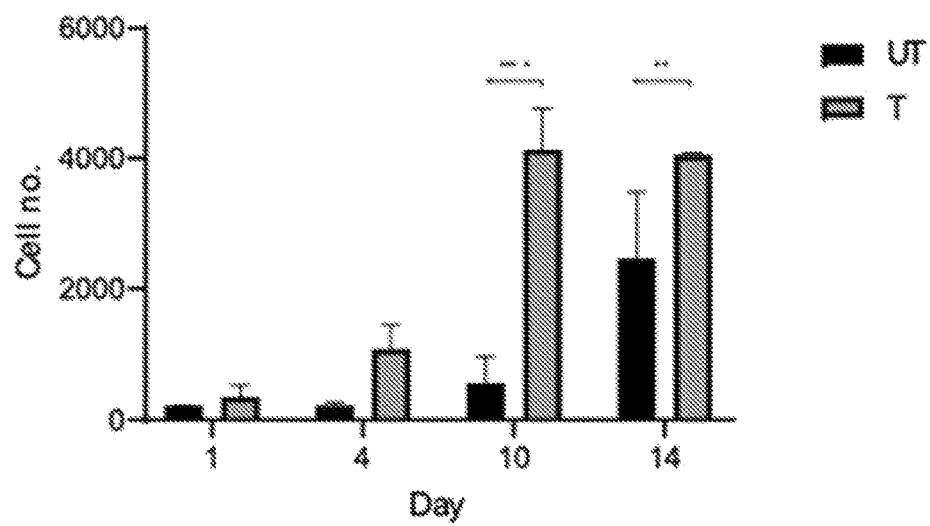

Seeded cells were observed to populate the edge of scaffolds, with no visible differences between the untreated and PIII-treated materials on day 1 (FIG. 33A). By day 7, hMSCs have populated the central part of treated scaffolds, with visibly more cells on treated scaffolds compared to untreated scaffolds. This trend of increased cell growth on treated scaffolds persisted until day 14, by which time treated scaffolds displayed highly confluent cell layers while significant gaps were still present on the untreated materials. Quantification of cell numbers confirmed significantly increased MSC proliferation on treated scaffolds compared to untreated controls on days 10 and 14 (FIG. 33 B).

What is claimed is:

1. A method for plasma modification of a porous material, comprising:
 a) flowing a gas into pores of said porous material; and
 b) exposing the gas to a pulsed electric field in said pores;
 wherein
  the porous material is a three-dimensional structure and has a plurality of internal cavities; and
  the pulsed electric field is provided by a powered first electrode with sufficient strength to ionise the gas to generate a plasma, wherein
   the powered first electrode at least partially surrounds the porous material; and
   the ionization of the gas occurs inside the plurality of internal cavities of the porous material;
   the porous material is held within a support and the support is in the form of a sleeve or tube that constrains the flow of the gas; and
   the powered first electrode is the sleeve or tube or at least partially surrounds the sleeve or tube.

2. The method of claim 1 wherein the gas is passed continuously through said pores during step b).

3. The method of claim 1 comprising step c), after step b), of exposing the functionalised porous material to a functional species in solution so as to covalently attach said functional species to the surfaces of the pores.

4. The method of claim 3 wherein the functional species is a labelling molecule, a bioactive molecule, a biological molecule, a cell, a micelle, a liposome, a polymer particle, a hydrogel or a nanoparticle.

5. The method of claim 1 wherein the gas includes at least one element of nitrogen, carbon and argon.

6. The method of claim 1 wherein the mean pressure of the gas in Torr within the porous material during step b) is $k/d$, where k has a value between about $10^{-5}$ and about $10^{-1}$ in units of Torr·m and d is the diameter of the smallest pore to be functionalised.

7. The method of claim 1 wherein a downstream pressure of the gas is less than about 5 mTorr.

8. The method of claim 1 wherein the pulsed electric field has pulses of about 5 to about 500 microseconds in duration.

9. The method of claim 1 wherein the pores of the porous material have a mean diameter of about 0.1 to about 1000 microns.

10. The method of claim 1 wherein the pulsed electric field is generated by a potential between the powered first electrode and an earthed second electrode, wherein the earthed second electrode is remote from the porous material.

11. The method of claim 10 wherein the earthed second electrode either forms part of a containment vessel in which the powered first electrode and the porous material are located or is disposed on a wall of the containment vessel.

12. A method of plasma modification of a porous material that is a three-dimensional structure, the method comprising:
 locating the porous material in an electric field so as to impart to the internal and external surfaces of the porous material an electric potential, including:
  placing at least a powered first electrode around the porous material so that there is a straight line between two points on the powered first electrode which passes through some point in the porous material;
 generating, from a gas provided within the porous material, a plasma at the porous material, wherein the plasma is an electrically conductive medium between the electrodes; and
 providing the gas at pressure that results in ions of the plasma implanting in the porous material under the force of the electric field;
 wherein the porous material is held within a support and the support is in the form of a sleeve or tube that constrains the gas at pressure and wherein the powered first electrode is the sleeve or tube or at least partially surrounds the sleeve or tube.

13. The method of claim 12, wherein the step of locating the porous material in the electric field further includes placing at least a second electrode remote from the porous material, wherein
 the second electrode is earthed; and
 at least part of the electric field is generated between the powered first electrode and the second electrode.

14. The method of claim 13, wherein the second electrode either forms part of a containment vessel in which the powered first electrode and the porous material are located or is disposed on a wall of the containment vessel.

15. The method of claim 12, wherein the pulsed electrical field has a pulsed DC waveform.

16. The method of claim 12, wherein the gas includes at least one element of nitrogen, carbon and argon.

* * * * *